US012558008B2

(12) United States Patent
Haneda et al.

(10) Patent No.: US 12,558,008 B2
(45) Date of Patent: Feb. 24, 2026

(54) HIGH MOLECULAR WEIGHT REDOX POLYMER AND BIOSENSOR USING SAME

(71) Applicant: PHC Holdings Corporation, Tokyo (JP)

(72) Inventors: Keigo Haneda, Ehime (JP); Kazuaki Edagawa, Ehime (JP); Fumihisa Kitawaki, Ehime (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 913 days.

(21) Appl. No.: 17/764,842

(22) PCT Filed: Sep. 30, 2019

(86) PCT No.: PCT/JP2019/038464

§ 371 (c)(1),
(2) Date: Mar. 29, 2022

(87) PCT Pub. No.: WO2021/064774

PCT Pub. Date: Apr. 8, 2021

(65) Prior Publication Data

US 2022/0322978 A1 Oct. 13, 2022

(51) Int. Cl.
*A61B 5/1486* (2006.01)
*A61B 5/145* (2006.01)
*C12Q 1/32* (2006.01)

(52) U.S. Cl.
CPC ...... *A61B 5/14865* (2013.01); *A61B 5/14532* (2013.01); *A61B 5/14546* (2013.01); *C12Q 1/32* (2013.01)

(58) Field of Classification Search
CPC ............ A61B 5/14532; A61B 5/14546; A61B 5/1486; A61B 5/14865; C08G 69/10; C08G 69/48; C08G 73/0206; C12Q 1/006; C12Q 1/32; Y02E 60/50
See application file for complete search history.

(56) References Cited

U.S. PATENT DOCUMENTS

| | | | |
|---|---|---|---|
| 2005/0164329 A1 | 7/2005 | Wallace-Davis et al. | |
| 2006/0069211 A1 | 3/2006 | Liu et al. | |
| 2009/0246808 A1 | 10/2009 | Wilsey et al. | |
| 2011/0290670 A1 | 12/2011 | Wilsey et al. | |
| 2017/0226068 A1 | 8/2017 | Heindl et al. | |
| 2021/0025843 A1 | 1/2021 | Haneda et al. | |

FOREIGN PATENT DOCUMENTS

| | | | |
|---|---|---|---|
| CN | 102046805 | 7/2013 | |
| CN | 106164054 | 11/2016 | |
| CN | 111936050 | 11/2020 | |
| EP | 3 777 683 | 2/2021 | |
| JP | 61-87676 | 5/1986 | |
| JP | 10-291368 | 11/1998 | |
| JP | 2006-131893 | 5/2006 | |
| JP | 2011-515686 | 5/2011 | |
| JP | 2013-164426 | 8/2013 | |
| JP | 2014-194411 | 10/2014 | |
| JP | 2016-122519 | 7/2016 | |
| JP | 2017-517480 | 6/2017 | |
| WO | WO-2005052589 A1 * | 6/2005 | ............... C12Q 1/32 |

(Continued)

OTHER PUBLICATIONS

International Search Report issued Dec. 3, 2019 in International (PCT) Application No. PCT/JP2019/038464.
International Search Report issued Mar. 19, 2019 in International (PCT) Application No. PCT/JP2019/002805.
Notice of Allowance issued Aug. 30, 2023, in U.S. Appl. No. 17/043,086.
European Search Report issued May 24, 2023, in European Application No. 19947973.4.
Winsberg et al., "TEMPO/Phenazine Combi-Molecule: A Redox-Active Material for Symmetric Aqueous Redox-Flow Batteries", ACS Energy Letters, 2016, vol. 1, pp. 976-980.

*Primary Examiner* — Ana L. Woodward
(74) *Attorney, Agent, or Firm* — Wenderoth, Lind & Ponack, L.L.P.

(57) ABSTRACT

The present disclosure provides a means for preventing or suppressing the leaching of a redox mediator constituting a reagent layer in a probe of an embedded biosensor, in particular, a means capable of improving preservation stability (durability) while maintaining glucose measurement sensitivity. The high molecular weight redox polymer according to the present disclosure is represented by general formula (A1), wherein $X^-$ represents an anionic species; L represents a linker; Poly represents a high molecular weight polymer; and $R^1$ to $R^8$ each independently represent a hydrogen atom or a substituent. The biosensor according to the present disclosure has a working electrode, a counter electrode, a reagent layer disposed on the working electrode, and a protective film covering at least the reagent layer, and the reagent layer contains an oxidoreductase that oxidizes or dehydrogenates the analyte and at least one high molecular weight redox polymer represented by general formula (A1).

(A1)

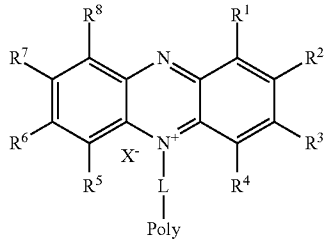

23 Claims, 10 Drawing Sheets

(56) References Cited

FOREIGN PATENT DOCUMENTS

| | | |
|---|---|---|
| WO | 2018062542 | 4/2018 |
| WO | 2019/187586 | 10/2019 |

* cited by examiner

[Figure 1]
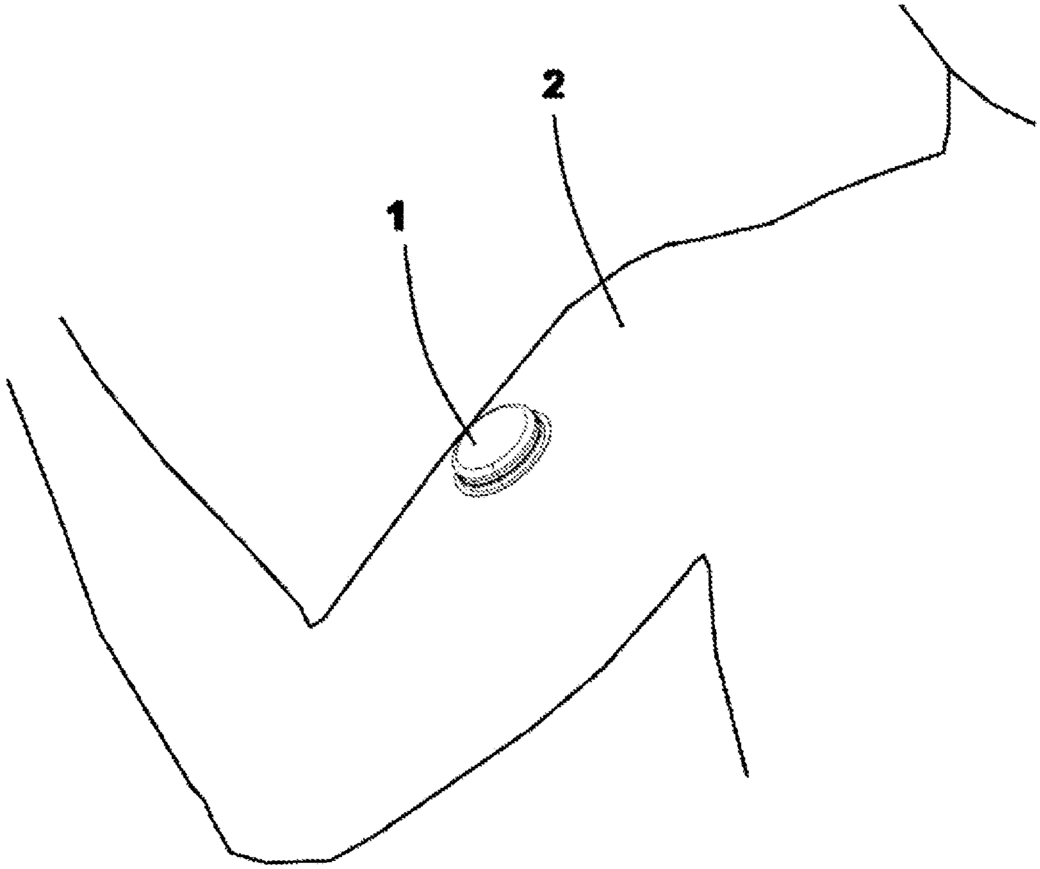

[Figure 2]
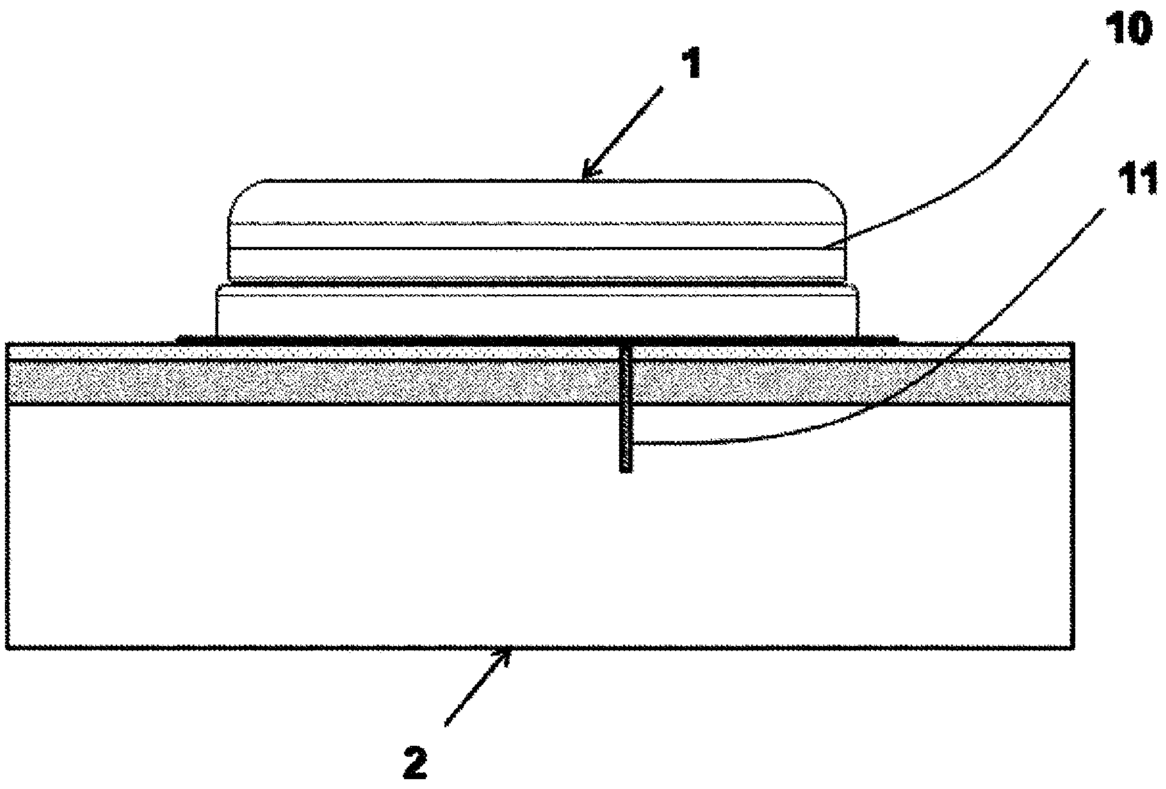
[Figure 3]
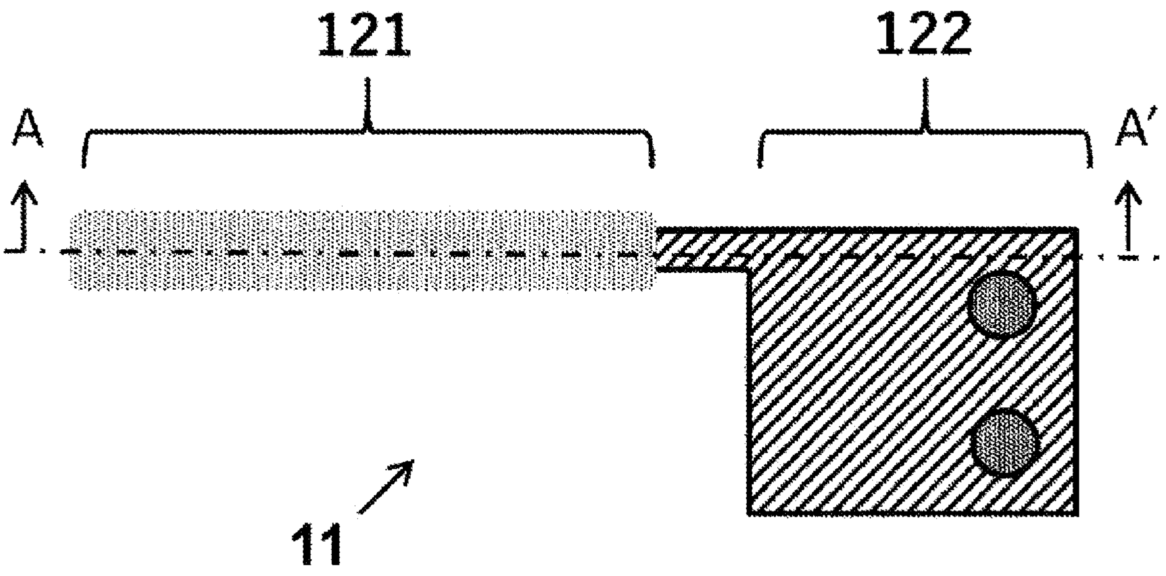

[Figure 4]
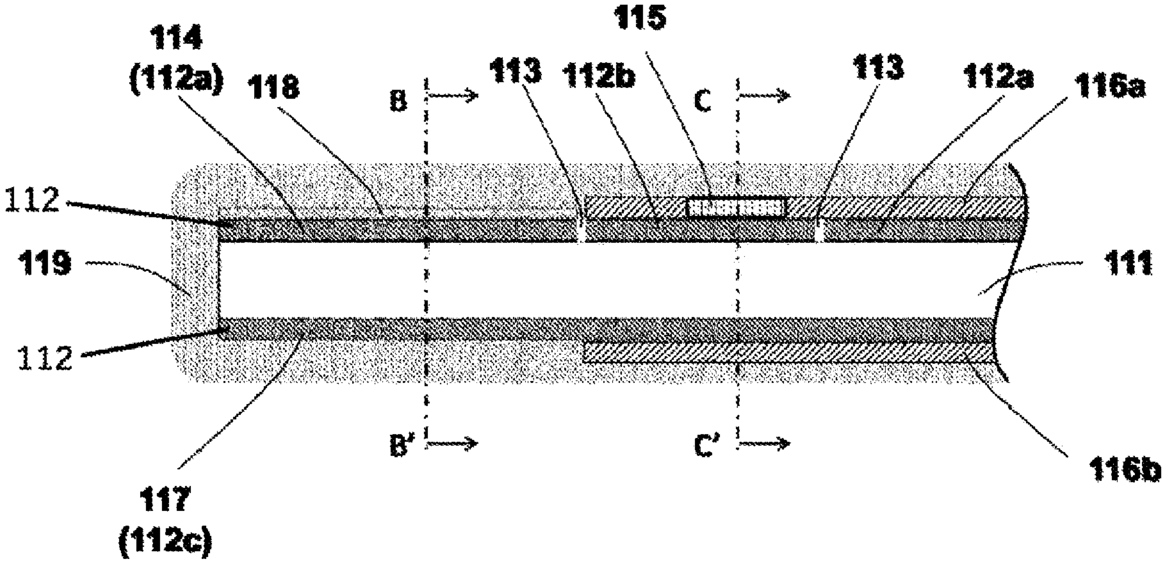
[Figure 5]
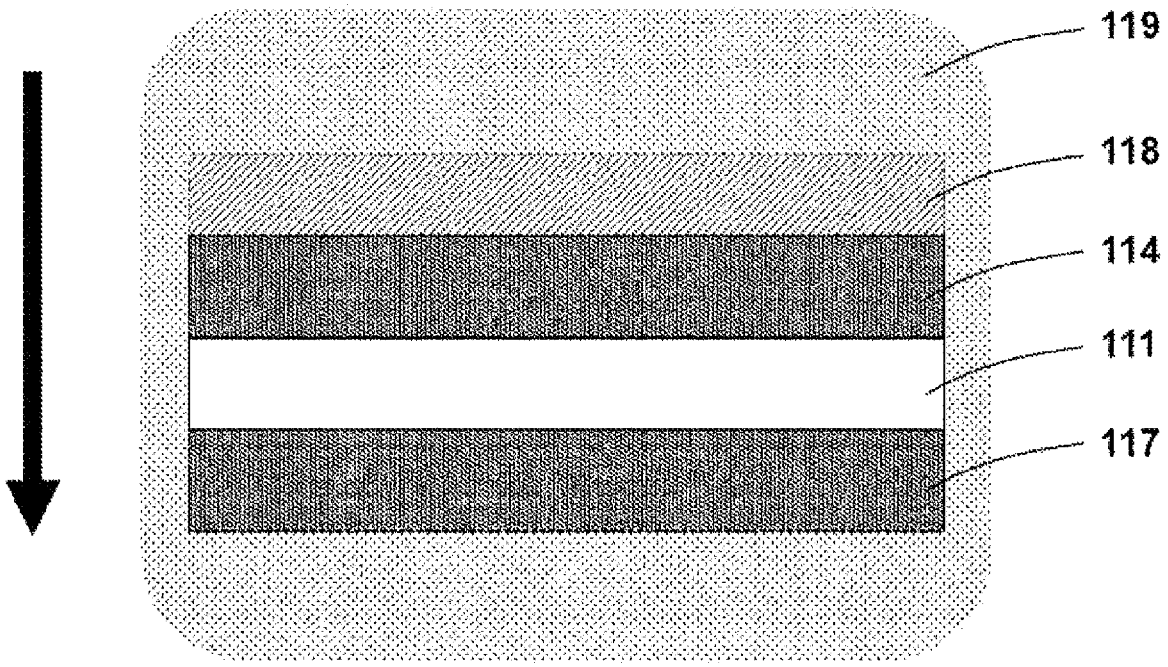

HIGH MOLECULAR WEIGHT REDOX POLYMER AND BIOSENSOR USING SAME

TECHNICAL FIELD

The present disclosure relates to a high molecular weight redox polymer and a biosensor using the same. More specifically, the present invention relates to a biosensor embedded in a living body.

BACKGROUND ART

A representative example of an electrochemical biosensor using an enzyme is an electrochemical glucose sensor for self-monitoring of blood glucose levels. Electrochemical glucose sensors use a glucose oxidoreductase. Examples of the glucose oxidoreductase include glucose oxidase (Gox) and glucose dehydrogenase (GDH).

In recent years, embedded electrochemical glucose sensors have been developed to measure glucose levels in a living body continuously or semi-continuously. As shown in FIGS. 1 and 2, such an embedded electrochemical glucose sensor measures glucose levels in blood or an interstitial fluid continuously or semi-continuously by placing a main body 10 on the living body 2 and inserting a probe 11 into the living body.

Embedded electrochemical biosensors represented by such an embedded electrochemical glucose sensor place their probe in a living body for a long time (commonly for days to weeks). Therefore, a reagent layer containing an oxidoreductase and a redox mediator (an electron transmitter), which is disposed on an electrode, is coated with a protective film. This structure prevents or suppresses a risk of leaching of an oxidoreductase or a redox mediator out of the sensor. If the oxidoreductase or the redox mediator leaches out of the sensor, not only the measurement sensitivity is deteriorated, but also the living body may be harmed, and the durability of the sensor is degraded.

For example, Patent Literature 1 discloses an ionic hydrophilic high molecular weight redox polymer for an enzyme-based electrochemical sensor. Patent Literatures 2 to 6 disclose phenazine compounds having a substituent, for example, at the 5- or 1-position of phenazine (e.g., 1-methoxy-5-methylphenazinium salts) as electron mediators of a biosensor. Patent Literature 7 discloses phenazine compounds having a substituent at the 5-position or the like of phenazine.

CITATION LIST

Patent Literatures

Patent Literature 1: JP 2006-131893 A
Patent Literature 2: JP 2014-194411 A
Patent Literature 3: JP 2016-122519 A
Patent Literature 4: JP 2013-164426 A
Patent Literature 5: JP 2011-515686 A
Patent Literature 6: JP 1986(S61)-87676 A
Patent Literature 7: JP 1998(H10)-291368 A

SUMMARY OF INVENTION

Technical Problem

As described above, it is important for an embedded electrochemical biosensor to have measures to prevent or suppress leaching of an oxidoreductase or a redox mediator out of a reagent layer through a protective layer. The object of the present disclosure is to provide means that can prevent or suppress the leaching of a redox mediator constituting a reagent layer in a probe of an embedded biosensor and can improve the preservation stability (durability) while maintaining the sensitivity of measuring an analyte (e.g., glucose).

Solution to Problem

The present inventors found that, when a phenazine compound is selected as a redox mediator, and a linker is introduced into the phenazine compound (i.e., derivatized) at a nitrogen atom at the 5-position thereof, various high molecular weight polymers (e.g., synthetic resins, proteins) can be linked via the linker while maintaining excellent performance as a redox mediator of the phenazine compound, and that the leaching can be better prevented or suppressed by adding the thus obtained high molecular weight redox polymer to a reagent layer, as compared with when a phenazine compound is solely added to the reagent layer.

Specifically, the present invention encompasses at least the following items:

[1]

A high molecular weight redox polymer represented by general formula (A1):

[Formula 1]

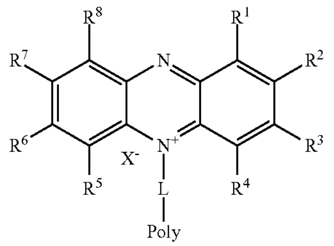

(A1)

wherein $X^-$ represents an anionic species; L represents a linker; Poly represents a high molecular weight polymer; and $R^1$ to $R^8$ each independently represent a hydrogen atom, a halogen atom, a hydroxyl group, a carboxyl group, an amino group optionally having a substituent, a linear or branched, saturated or unsaturated hydrocarbon group having 1 to 6 carbon atoms and optionally having a substituent, an acyl group optionally having a substituent, an alkoxy group optionally having a substituent, or a phenyl group optionally having a substituent.

[2]

The high molecular weight redox polymer according to item 1, which is represented by general formula (B1):

[Formula 2]

(B1)

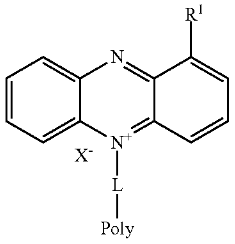

wherein $X^-$ represents an anionic species; L represents a linker; Poly represents a high molecular weight polymer; and $R^1$ represents a hydrogen atom, a halogen atom, a hydroxyl group, a carboxyl group, an amino group optionally having a substituent, a linear or branched, saturated or unsaturated hydrocarbon group having 1 to 6 carbon atoms and optionally having a substituent, an acyl group optionally having a substituent, an alkoxy group optionally having a substituent, or a phenyl group optionally having a substituent.

[3]

The high molecular weight redox polymer according to item 1 or 2, which is represented by general formula (1):

[Formula 3]

(1)

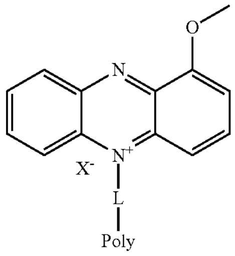

wherein $X^-$ represents an anionic species; L represents a linker; and Poly represents a high molecular weight polymer.

[4]

The high molecular weight redox polymer according to any one of items 1 to 3, wherein in the linker, at least one atom selected from the group consisting of a carbon atom, a nitrogen atom, an oxygen atom, and a sulfur atom constitutes a main chain in which a plurality of the atoms bonds in a chain.

[5]

The high molecular weight redox polymer according to any one of items 1 to 4, which is represented by general formula (2):

[Formula 4]

(2)

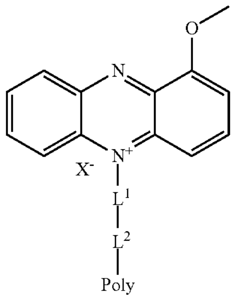

wherein $X^-$ represents an anionic species; $L^2$ represents a first linker; $L^2$ represents a second linker; and Poly represents a high molecular weight polymer.

[6]

The high molecular weight redox polymer according to item 5, wherein the first linker and the second linker are bonded by a covalent bond.

[7]

The high molecular weight redox polymer according to item 5 or 6, wherein the first linker contains at least one of a polyethylene glycol chain and a hydrocarbon chain.

[8]

The high molecular weight redox polymer according to item 7, which is represented by general formula (3):

[Formula 5]

(3)

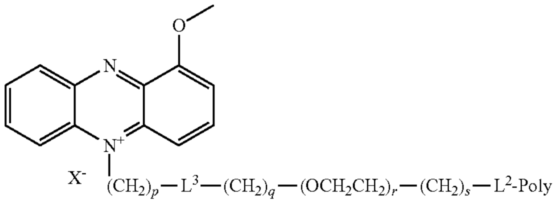

wherein $X^-$ represents an anionic species;

$L^3$ is not present or is —O—, —C(═O)—NH—, or —NH—C(═O)—;

$L^2$ represents the second linker;

Poly represents a high molecular weight polymer;

p, q, and s are each independently an integer of 1 to 15; and r is an integer of 0 to 80.

[9]

The high molecular weight redox polymer according to item 8, which is represented by general formula (4):

[Formula 6]

(4)

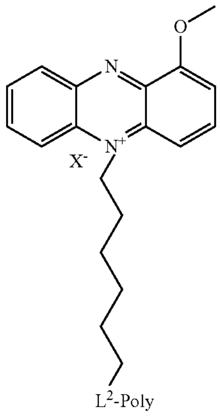

wherein $X^-$ represents an anionic species; $L^2$ represents the second linker; and Poly represents a high molecular weight polymer;

or general formula (5):

[Formula 7]

(5)

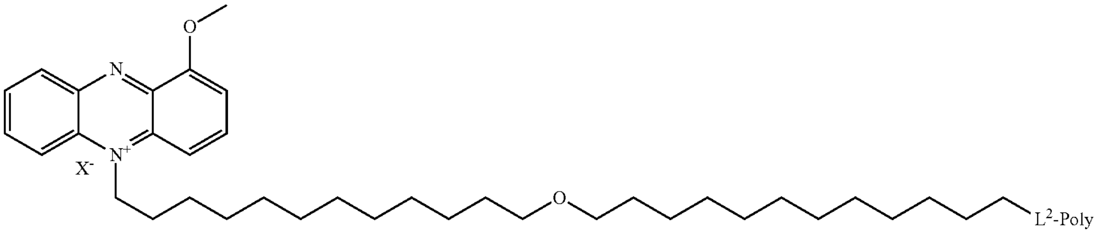

wherein $X^-$ represents an anionic species; $L^2$ represents the second linker; and Poly represents a high molecular weight polymer;

or general formula (6):

[Formula 8]

(6)

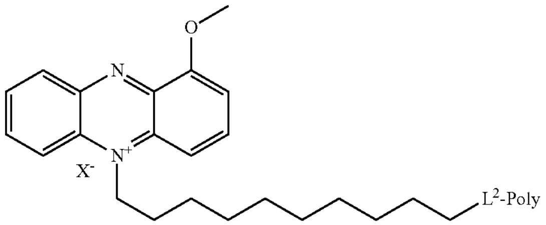

wherein $X^-$ represents an anionic species; $L^2$ represents the second linker; and Poly represents a high molecular weight polymer;

or general formula (7):

[Formula 9]

(7)

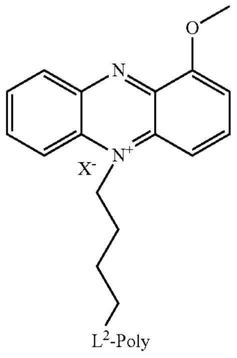

wherein $X^-$ represents an anionic species; $L^2$ represents the second linker; and Poly represents a high molecular weight polymer;

or general formula (8)

[Formula 10]

(8)

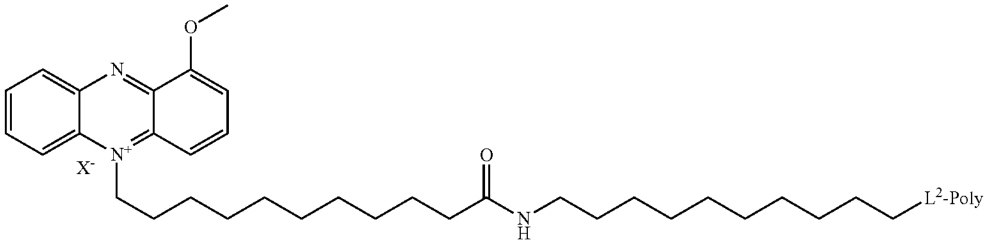

wherein $X^-$ represents an anionic species; $L^2$ represents the second linker; and Poly represents a high molecular weight polymer;

or general formula (9):

[Formula 11]

(9)

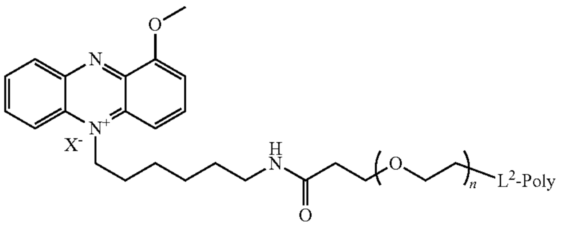

wherein $X^-$ represents an anionic species; $L^2$ represents the second linker; Poly represents a high molecular weight polymer; and n is an integer of 1 to 80.

[10]

The high molecular weight redox polymer according to any one of items 1 to 9, wherein in the high molecular weight polymer, at least one atom selected from the group consisting of a carbon atom, a nitrogen atom, an oxygen atom, and a sulfur atom constitutes a main chain in which a plurality of the atoms bonds in a chain.

[11]

The high molecular weight redox polymer according to item 10, wherein bonds between atoms constituting the high molecular weight polymer main chain include at least one selected from the group consisting of a carbon-carbon bond, an amide bond, and an ether bond.

[12]

The high molecular weight redox polymer according to item 10 or 11, wherein the high molecular weight polymer is a polyamino acid-based polymer, a polyimine-based polymer, or an ethylene-based polymer.

[13]

The high molecular weight redox polymer according to item 10 or 11, wherein the high molecular weight polymer is a protein, a polypeptide, or a polynucleotide.

[14]

The high molecular weight redox polymer according to any one of items 1 to 13, wherein the anionic species is any one selected from the group consisting of a halogen ion, an ion of a compound containing halogen, a hydroxide ion, a carboxylate ion, a nitrate ion, a nitrite ion, an acetate ion, a hydrogen carbonate ion, a dihydrogen phosphate ion, a hydrogen sulfate ion, an alkyl sulfonate ion, a hydrogen sulfide ion, a hydrogen oxalate ion, a cyanate ion, and a thiocyanate ion.

[15]

The high molecular weight redox polymer according to any one of items 1 to 14, which is hydrophilic.

[16]

A high molecular weight redox polymer mixture, comprising a plurality of types of high molecular weight redox polymers according to any one of items 1 to 15.

[17]

A biosensor for detecting or quantifying an analyte, comprising:

a working electrode, a counter electrode, a reagent layer disposed on the working electrode, and a protective film covering at least the reagent layer;

the reagent layer comprising an oxidoreductase that oxidizes or dehydrogenates the analyte and the high molecular weight redox polymer according to any one of items 1 to 15 or the high molecular weight redox polymer mixture according to item 16.

[18]

The biosensor according to item 17, which has a reference electrode.

[19]

The biosensor according to item 17 of 18, wherein the oxidoreductase is a coenzyme-binding enzyme.

[20]

The biosensor according to any one of items 17 to 19, wherein the analyte is glucose, and the oxidoreductase is glucose oxidase or glucose dehydrogenase.

[21]

The biosensor according to item 20, wherein the glucose dehydrogenase is a flavin adenine dinucleotide (FAD)-dependent glucose dehydrogenase.

[22]

The biosensor according to item 20 or 21, wherein the glucose dehydrogenase has an enzyme activity against maltose of 5% or lower when the enzyme activity against glucose is assumed to be 100%.

[23]

The biosensor according to item 20 or 21, wherein the glucose dehydrogenase has an enzyme activity against maltose of 3% or lower when the enzyme activity against glucose is assumed to be 100%.

[24]

The biosensor according to any one of items 19 to 23, wherein the oxidoreductase is crosslinked to the high molecular weight redox polymer.

[25]

The biosensor according to any one of items 17 to 24, wherein the protective film has a pore for allowing an analyte existing outside the protective film to permeate into

Advantageous Effects of Invention

Because the high molecular weight redox polymer and the biosensor using the same of the present disclosure has a redox mediator (a phenazine derivative) that is bonded to a high molecular weight polymer, the leaching of the redox mediator out of a protective film (leaching into a living body when the biosensor is embedded into the living body) can be prevented or suppressed better. As a result, preservation stability (durability) can be improved while measurement sensitivity is maintained.

BRIEF DESCRIPTION OF DRAWINGS

FIG. 1 is an example of a view showing an embedded biosensor in the state of being attached to a living body (human body).

FIG. 2 is an example of a cross-sectional view showing an embedded biosensor in the state of being attached to a living body (human body).

FIG. 3 is a top view showing the front side of an embedded biosensor probe, which is an example of the present disclosure.

FIG. 4 is a cross-sectional view by the A-A' cutting plane line in FIG. 3.

FIG. 5 is a cross-sectional view by the B-B' cutting plane line in FIG. 4.

DESCRIPTION OF EMBODIMENTS

Figure 6:
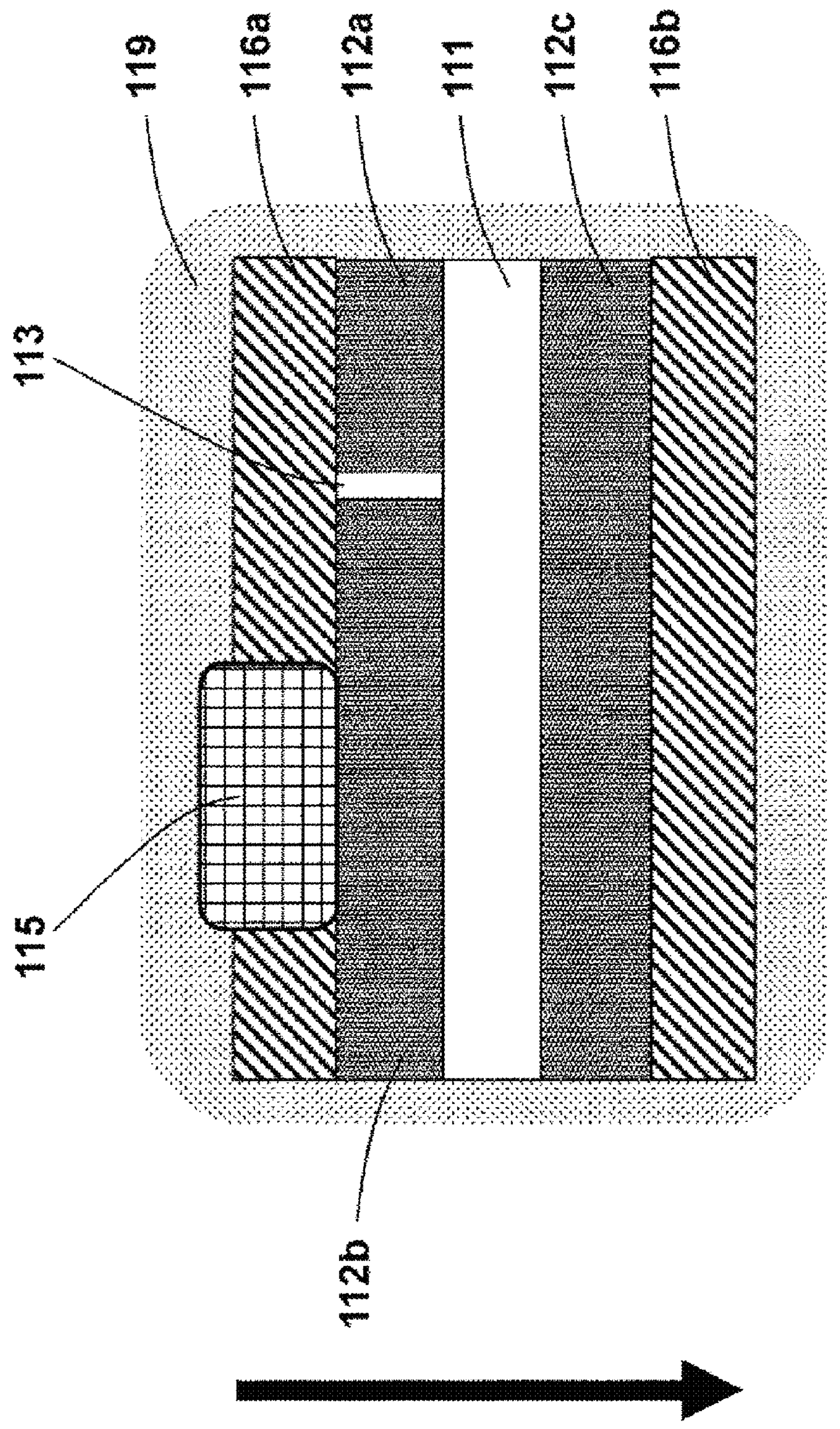
FIG. 6 is a cross-sectional view by the C-C' cutting plane line in FIG. 4.

Embodiments of the high molecular weight redox polymer and the biosensor using the same of the present disclosure are described in more detail.

—High Molecular Weight Redox Polymer—

The high molecular weight redox polymer of the present disclosure is a compound in which a phenazine compound, which is a redox mediator, is linked to a high molecular weight polymer via a linker bonded to a nitrogen atom at the 5-position thereof.

In the present disclosure, the term "redox mediator" means an oxidizing and reducing substance that mediates electron transmission. In a biosensor, the redox mediator refers to a substance responsible for electron transmission that occurs with an oxidation reduction reaction of an analyte catalyzed by an oxidoreductase. In the present disclosure, a "phenazine compound" having such a function, in particular, a "phenazine derivative" into which a linker is introduced at a nitrogen atom at the 5-position thereof is used as a redox mediator. Examples of the redox mediator include various compounds such as ferricyanides and ferrocene. Phenazine compounds are particularly preferred redox mediators since they are less susceptible to the effect of impurities such as ascorbic acid (vitamin C) and uric acid in a biological sample for electrochemical measurement because of their low redox potential, that is a negative redox potential below 0 V (vs. Ag/AgCl saturated KCl).

A "phenazine compound" is a compound which has a phenazine skeleton (see the formula below) and in which carbon atoms at the 1- to 4-positions and 6- to 9-positions may be substituted. Phenazine compounds are not particularly limited as long as they function as a redox mediator. As such phenazine compounds, various kinds of compounds are publicly known and can be used to prepare a high molecular weight redox polymer in the present invention.

[Formula 12]

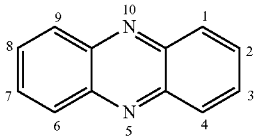

Phenazine skeleton

More specifically, the high molecular weight redox polymer of the present disclosure can be represented by general formula (A1):

[Formula 13]

(A1)

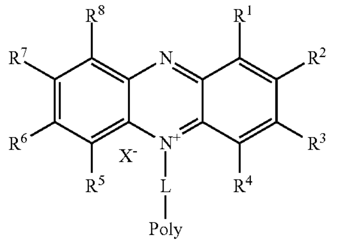

In general formula (A1), $X^-$ represents an anionic species; L represents a linker; and Poly represents a high molecular weight polymer.

In general formula (A1), $R^1$ to $R^8$ each independently represent, for example, (i) a hydrogen atom, (ii) a halogen atom, (iii) a hydroxyl group, (iv) a carboxyl group, (v) an amino group optionally having a substituent, (vi) a $C_{1-6}$ linear or branched, saturated or unsaturated hydrocarbon group (1 to 6 carbon atoms, lower alkyl) optionally having a substituent, (vii) an acyl group optionally having a substituent (e.g., $C_{1-6}$ alkyl-carbonyl group), (viii) an alkoxy group optionally having a substituent (e.g., $C_{1-6}$ alkoxy group), or (ix) a phenyl group optionally having a substituent. Examples of substituents which may be present in the above-mentioned (v), (vi), (vii), (viii), and (ix) include (a) a halogen atom, (b) a hydroxyl group, (c) a carboxyl group, (d) an amino group, (e) a $C_{1-6}$ (1 to 6 carbon atoms, lower alkyl) linear or branched, saturated or unsaturated hydrocarbon group, (f) an acyl group (e.g., $C_{1-6}$ alkyl-carbonyl group), (g) an alkoxy group (e.g., $C_{1-6}$ alkoxy group), (h) a carboxyl-alkyl group (e.g., carboxyl-$C_{1-6}$ alkyl group), (i) a mesyl group, and (k) a phenyl group. The number of substituents which may be present in the above-mentioned (v), (vi), (vii), (viii), and (ix) is not particularly limited and may be, for example, one, two, or three. Alternatively, a plurality of substituents may be bonded to one atom (e.g., a carbon atom of an alkyl group, a nitrogen atom of an amino group). $R^1$ to $R^8$ are not limited to the above-mentioned substituents and may be substituents which may be present in known phenazine compounds at respective positions.

Here, general formula (A1) apparently indicates that only one phenazine derivative is bonded to one high molecular weight polymer (Poly), but should not be interpreted in such a limited way. It should be interpreted that at least one, usually a plurality of phenazine derivatives are bonded to one high molecular weight polymer. Additionally, in such a manufacturing method as described in the present specification, in which a phenazine derivative and a high molecular weight polymer are allowed to react to generate a high molecular weight redox polymer, high molecular weight polymer compositions with distributions in the number of phenazine derivatives bonded to one high molecular weight polymer can be obtained. How the numbers of phenazine derivatives bonded to a high molecular weight polymer composition are distributed and the (mean) number of phenazine derivatives bonded to one high molecular weight polymer are not particularly limited, but can be adjusted suitably in consideration of purpose, performance, and the like, as well as depending on the raw materials (high molecular weight polymers or monomers constituting them), reaction conditions, and the like for manufacture of the high molecular weight redox polymer. For example, the number of the first or second reactive groups listed in Table 1 shown later contained in one monomer molecule (e.g., the second' linker portion) used as raw material of the high molecular weight polymer can be increased or decreased; the proportions of the corresponding reactive groups contained in a phenazine derivative (e.g., the first' linker portion) and the actually reacted groups among these reactive groups contained in the whole monomer can be increased or decreased depending on the reaction conditions; the (mean) number of bonded phenazine derivatives can be increased or decreased; and how the numbers are distributed can be changed. Therefore, a high molecular weight redox polymer (composition) having intended properties in which an intended number of phenazine derivatives are bonded to a high molecular weight polymer can be manufactured.

Anionic species are not particularly limited, and examples of the anionic species include any one selected from the group consisting of a halogen ion, an ion of a compound containing halogen, a hydroxide ion, a carboxylate ion, a nitrate ion, a nitrite ion, an acetate ion, a hydrogen carbonate ion, a dihydrogen phosphate ion, a hydrogen sulfate ion, an alkyl sulfonate ion, a hydrogen sulfide ion, a hydrogen oxalate ion, a cyanate ion, and a thiocyanate ion.

The high molecular weight redox polymer of the present disclosure is hydrophilic. The hydrophilic high molecular weight redox polymer mentioned herein refers to a polymer that has a high affinity for water and is therefore easily dissolved or mixed in water and a polar solvent, preferably a polymer that is easily dissolved or mixed in a solvent used for reaction with a phenazine derivative, so that progression of a reaction is not affected. Examples of the polar solvent include methanol, ethanol, 1-propanol, 2-propanol, 1-butanol, 2-butanol, 2-methyl-1-propanol, 2-methyl-2-propanol, formic acid, acetic acid, tetrahydrofuran, acetone, dioxane, methyl thyl ketone, ethyl acetate, acetonitrile, dimethyl formamide, and dimethyl sulfoxide. A high molecular weight redox polymer is formed by linking a phenazine derivative and a high molecular weight polymer via a linker, and either one of the phenazine derivative (including the first' linker portion described later) and the high molecular weight polymer (including the second' linker portion described later) may be hydrophobic. Specifically, it is sufficient that the finally synthesized high molecular weight redox polymer is hydrophilic.

In the linker of the present disclosure, at least one atom selected from the group consisting of a carbon atom, a nitrogen atom, an oxygen atom, and a sulfur atom constitutes a main chain in which a plurality of the atoms bonds in a chain. Examples thereof include a hydrocarbon group that may contain an ether bond, a thioether bond, an amide bond, or the like (bonds containing a heteroatom) anywhere within the linker as a group generated by a reaction of a first reactive group and a second reactive group described later or as a group that has formed beforehand.

The main chain constituted by "at least one atom selected from the group consisting of a carbon atom, a nitrogen atom, an oxygen atom, and a sulfur atom in which a plurality of the atoms bonds in a chain" mentioned herein includes not only an open-chain compound (an acyclic compound), which refers to a linear compound having a molecular structure with no ring (a structure derived from a cyclic compound, a cyclic structure), but also a compound having a ring in parts thereof. Examples of a main chain containing a ring include a main chain having a group derived from an open-chain compound (e.g., an alkyl group) on one side of the ring (e.g., on one carbon atom in a benzene ring) and a group derived from an open-chain compound in the other side thereof (e.g., a carbon atom at the ortho, meta, or para position relative to a carbon atom to which the straight chain group is bonded) as well. In this case, the main chain is bonded to the phenazine derivative on one open-chain compound side (e.g., an alkyl group is converted to an alkylene group) and bonded to the high molecular weight polymer on the other open-chain compound side. One or both of the above-described two groups derived from an open-chain compound that are bonded via a ring flanked thereby can be replaced with a group derived from a compound having a ring in parts thereof. In addition, a side chain may be bonded to a main chain in the linker.

The description of the above-described "linker" is applicable not only to an explanation of "L" in general formula (A1), but also an explanation of each of "$L^1$" (a first linker) and "$L^2$" (a second linker), and "$L^1$-$L^2$," which is formed by binding $L^1$ and $L^2$ in general formula (A2) described below, as well as "$L^2$" (a second linker) in general formulas (A3) to (A9). It should be noted that $L^1$ and $L^2$ are linkers that are different from each other. For example, they are linkers containing different repeating units.

From viewpoints of improving the thermostability of a redox mediator (a phenazine derivative) in a biological environment, the number of atoms (the sum of the numbers of carbon atoms, nitrogen atoms, oxygen atoms, and sulfur atoms) constituting the main chain of a linker (e.g., "L" in general formula (A1), whole "$L^1$-$L^2$" in general formula (A2), or corresponding sites in Examples (A3) to (A9)) is preferably 10 or more, preferably 31 or more, yet more preferably 55 or more. The number of atoms constituting the main chain of the linker is preferably fewer than 720, preferably fewer than 340, yet more preferably fewer than 240.

The high molecular weight redox polymer represented by general formula (A1) is preferably represented by general formula (B1).

[Formula 14]

(B1)

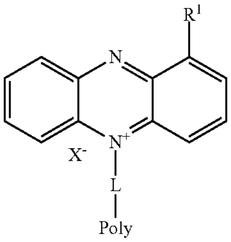

In general formula (B1), each symbol has the same meaning as each corresponding symbol in general formula (A1).

In other words, general formula (B1) corresponds to an embodiment specifying that $R^7$ and $R^8$ are both a hydrogen atom (unsubstituted), and only $R^1$ may be either a hydrogen atom (unsubstituted) or a predetermined substituent in general formula (A1).

The high molecular weight redox polymer represented by general formula (A1) or (B1) is particularly preferably represented by general formula (1).

[Formula 15]

(1)

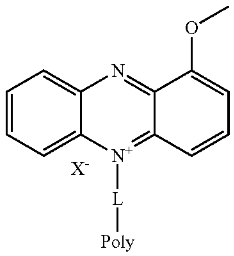

In general formula (1), each symbol has the same meaning as each corresponding symbol in general formula (A1). In other words, general formula (1) corresponds to an embodiment specifying that $R^7$ and $R^8$ are both a hydrogen atom (unsubstituted), and $R^1$ is a methoxy group (an alkoxy group) in general formula (A1).

The linker contained in the high molecular weight redox polymer of the present disclosure is preferably formed by binding two different linkers, i.e., a first linker and a second linker.

A high molecular weight redox polymer having such a linker can be represented as general formula (A2), for example, wherein the linker (L) is replaced with a first linker and a second linker that are bonded to each other (-$L^1$-$L^2$-) in general formula (A1).

[Formula 16]

(A2)

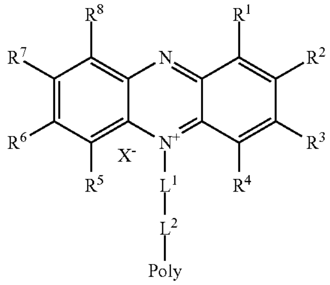

In general formula (A2), $L^1$ represents a first linker; $L^2$ represents a second linker; and each of other symbols has the same meaning as each corresponding symbol in general formula (A1).

In general formula (A2), the site ($L^1$-$L^2$) at which the first linker and the second linker are bonded to each other corresponds to a site of a linker (L) in general formula (A1).

In the present disclosure, the first linker and the second linker are preferably bonded by a covalent bond. However, the first linker and the second linker may be bonded by a noncovalent bond (e.g., electrostatic interaction) as long as the effect of the present invention is exhibited.

The covalent bond formed at the site at which the first linker and the second linker are bonded is not particularly limited, and examples thereof include a covalent bond formed by a reaction of a first reactive group (a univalent group derived from the compounds listed in the table, such as amine, in particular, an amino group at the end thereof or the like) and a second reactive group (a univalent group derived from the compounds listed in the table, such as carboxylic acid, in particular, a carboxyl group at the end thereof or the like) listed in Table 1 shown below. Such covalent bonds and reactive groups for forming covalent bonds are well known to and commonly used by those skilled in the art (e.g., Japanese Translation of PCT International Application Publication No. 2003-514924). The first reactive groups and the second reactive groups listed in Table 1 constitute the terminal portions of the first linker before bonded (hereinafter may be referred to as "first' linker") and the second linker before bonded (hereinafter may be referred to as "second' linker"). One of the first' linker and the second' linker has a first reactive group, and the other has a second reactive group. The second linker ($L^2$) in the general formula (2) and the below-described general formulas (3) to (9) contains atoms at the binding site generated by a reaction of the first reactive group and the second reactive group and atoms at sites that have not been changed by the reaction. For example, amine (amino group: $—NH_2$) is present at the end of the first' linker of a phenazine derivative as the firs' reactive group, and carboxylic acid (carboxyl group: —COOH) is present at the end of the second' linker of a high molecular weight polymer as the second reactive group. When these groups are allowed to react to generate an amide bond (—NH—CO—), the second linker represented by $L^2$ in general formula (3) contains atoms of —NH—CO—.

TABLE 1

| Binding site of the first linker and the second linker | First reactive group (groups derived from the following compounds) | Second reactive group (groups derived from the following compounds) |
|---|---|---|
| Amide | Amine | Carboxylic acid |
| | Amine | Activated ester |
| | Amine | Acyl azide |
| | Amine | Acyl halide |
| | Amine | Acid anhydride |
| Ether | Alcohol or phenol | Alkyl halide |
| | Alcohol or phenol | Alkyl sulfonate |
| Thioether | Thiol | Maleimide |
| | Thiol | Epoxide |
| | Thiol | Alkyl halide |
| | Thiol | Alkyl sulfonate |
| | Thiol | Aziridine |
| Ester | Alcohol or phenol | Carboxylic acid |
| | Carboxylic acid | Alkyl halide |
| | Alcohol or phenol | Acyl halide |
| | Alcohol or phenol | Acid anhydride |
| Thioester | Thiol | Carboxylic acid |
| Hydrazone | Hydrazine | Aldehyde or ketone |
| Urea | Amine | Isocyanate |
| Thiourea | Amine | Isothiocyanate |
| Oxime | Alkoxyamine | Aldehyde or ketone |
| | Hydroxyamine | Aldehyde or ketone |
| Amidine | Amine | Imidoester |
| Alkylamine | Amine | Epoxide |
| | Amine | Alkyl halide |
| Urethane | Alcohol or phenol | Isocyanate |
| Imidazolium | Imidazole | Epoxide |
| | Imidazole | Alkyl halide |
| | Imidazole | Alkyl sulfonate |
| Pyridinium | Pyridine | Epoxide |
| | Pyridine | Alkyl halide |
| | Pyridine | Alkyl sulfonate |
| Sulfonamide | Amine | Sulfonyl halide |
| Sulfonic aid ester | Alcohol or phenol | Sulfonyl halide |

* Examples of an activated ester include succinimidyl, benzotriazole, or aryl esters substituted with an electron-withdrawing group such as sulfo, nitro, or halo; and carboxylic acid esters activated by carbodiimide.

In one embodiment of the high molecular weight redox polymer of the present disclosure, a phenazine derivative and a high molecular weight polymer are linked by an amide bond. That is, a first' linker or another site of the phenazine derivative and a second' linker or another site of the high molecular weight polymer are linked by an amide bond generated by a reaction of a first reactive group (amine) corresponding to "amide" in Table 1 and a second reactive group (e.g., carboxylic acid, activated ester).

In one embodiment of the high molecular weight redox polymer of the present disclosure, a phenazine derivative and a high molecular weight polymer are linked by a covalent bond that is not an amide bond. That is, a first' linker or another site of the phenazine derivative and a second' linker or another site of the high molecular weight polymer are linked by a covalent bond generated by a reaction of a first reactive group and a second reactive group corresponding to each of "ether," "thioether," "ester," "thioester," "hydrazone," "urea," "thiourea," "oxime," "amidine," "alkylamine," "urethane," "imidazolium," "pyridinium," "sulfonamide," and "sulfonic acid ester" in Table 1.

When a protein, a polypeptide, or a polyamino acid is used as a high molecular weight polymer, a first reactive group and a second reactive group listed in Table 1 may be those which a side chain of amino acid residues constituting the protein or the like may have, or a linker separately introduced into the protein (a second' linker) may have. For example, lysine, arginine, and histidine correspond to amino acids having "amine" (an amino group) as the above-mentioned "first reactive group," aspartic acid and glutamic acid correspond to amino acids having "carboxylic acid" (a carboxyl group) as the above-mentioned "first reactive group" or "second reactive group," and cysteine corresponds to an amino acid having "thiol" (a sulfanyl group) as the above-mentioned "first reactive group." Therefore, a protein or a polypeptide containing these amino acid residues have their respective first reactive group or second reactive group and can form a covalent bond by reacting with a predetermined corresponding reactive group of the phenazine derivative under predetermined reaction conditions. Further, when a polynucleotide is used as a high molecular weight polymer, an unnatural, modified nucleotide used as a part of nucleotides constituting the polynucleotide may have the first reactive group and the second reactive group, or a linker separately introduced into the polynucleotide by other means (a second' linker) may have the first reactive group and the second reactive group. The method of forming a covalent bond with other reactive groups of another compounds (the phenazine derivative in the present disclosure) via an (introduced) reactive group of a protein, a polypeptide, or a polynucleotide is also known to and commonly used by those skilled in the art.

The first linker preferably constitutes such a main chain as described above, and examples thereof include a first linker containing at least one of a polyethylene glycol chain and a hydrocarbon chain. For example, the first linker in general formula (2) can be a linker represented at a site corresponding to the first linker in the general formulas (3) to (9) shown below.

Specific examples of the high molecular weight redox polymer represented by general formula (A2) include a high molecular weight redox polymer represented by general formula (A3):

[Formula 17]

(A3)

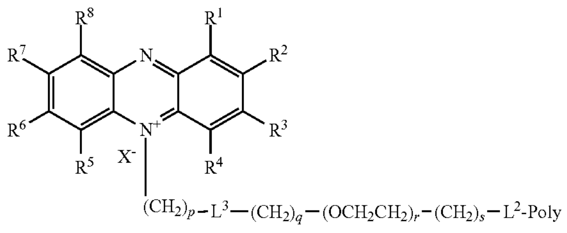

In general formula (A3), $L^3$ is not present or is —O—, —C(═O)—NH—, or —NH—C(═O)—;

$L^2$ represents the second linker;

p, q, and s are each independently an integer of 1 to 15;

r is an integer of 0 to 80, for example, 0 to 30; and each of other symbols has the same meaning as each corresponding symbol in general formula (A1).

Specific examples of the high molecular weight redox polymer represented by general formula (A3) include a high molecular weight redox polymer represented by any of general formulas (A4) to (A9).

[Formula 18]

(A4)

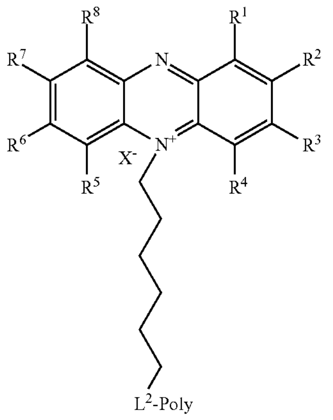

In general formula (A4), $L^2$ represents the second linker; and each of other symbols has the same meaning as each corresponding symbol in general formula (A1).

[Formula 19]

(A5)

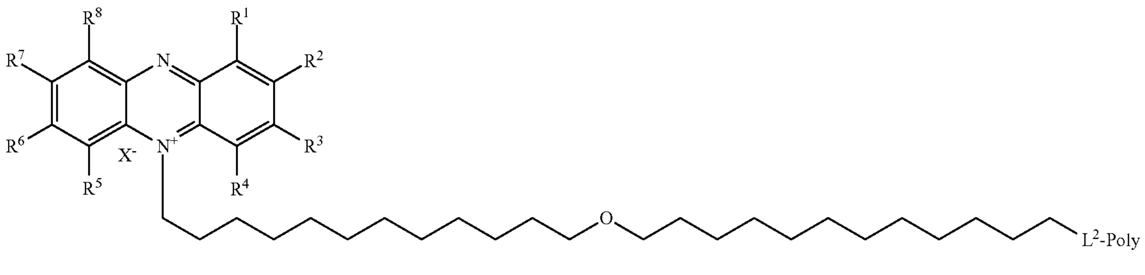

In general formula (A5), $L^2$ represents the second linker; and each of other symbols has the same meaning as each corresponding symbol in general formula (A1).

[Formula 20]

(A6)

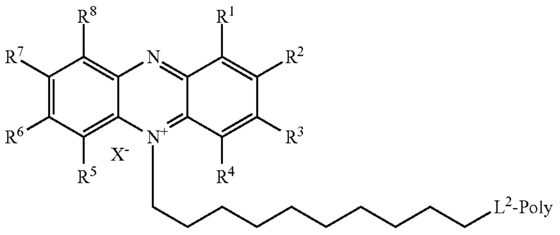

In general formula (A6), $L^2$ represents the second linker; and each of other symbols has the same meaning as each corresponding symbol in general formula (A1).

[Formula 21]

(A7)

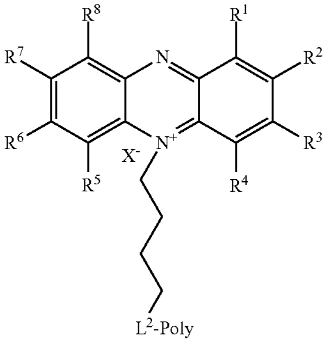

In general formula (A7), $L^2$ represents the second linker; and each of other symbols has the same meaning as each corresponding symbol in general formula (A1).

[Formula 22]

(A8)

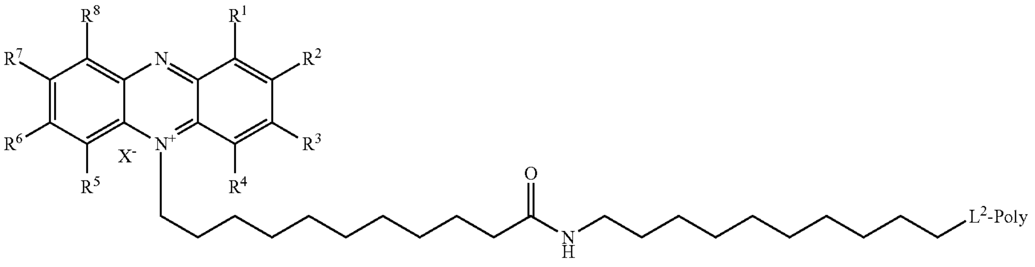

In general formula (A8), $L^2$ represents the second linker; and each of other symbols has the same meaning as each corresponding symbol in general formula (A1).

[Formula 23]

(A9)

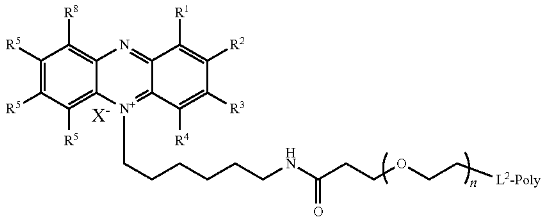

In general formula (A9), $L^2$ represents the second linker; n is an integer of 1 to 80, for example, 1 to 30; and each of other symbols has the same meaning as each corresponding symbol in general formula (A1).

Of note, general formulas (B) and (1) can also specify general formulas (B2) and (2) as high molecular weight redox polymers corresponding to general formula (A2) by replacing their respective linker (L) with a first linker and a second linker that are bonded to each other ($-L^1-L^2-$). Further, the above-mentioned general formulas (B2) and (2) can similarly specify general formulas (B3) to (B9) and general formulas (3) to (9) as the high molecular weight redox polymer corresponding to general formula (A3) mentioned as a specific example of general formula (A2) and the polymer redox polymers corresponding to general formulas (A4) to (A9) mentioned as specific examples of general formula (A3). In general formulas (B2) to (B9) and (2) to (9), $R^1$ to $R^8$, which are the substituents of the phenazine compound, have the same meaning as those in general formulas (A1) and (A2), and other symbols have the same meaning as the corresponding symbols in general formulas (A2) to (A9).

[Formula 24-1]

(B2)

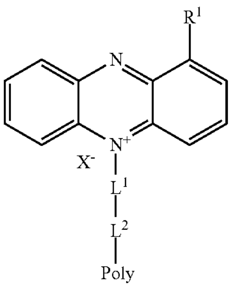

(B3)

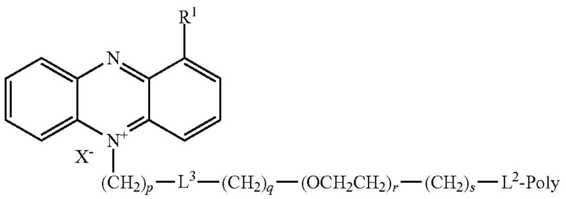

-continued
(B4)
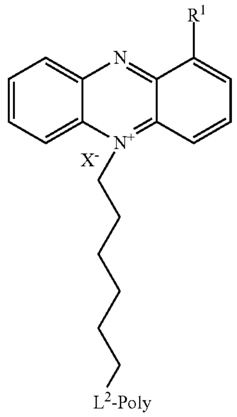
(B5)
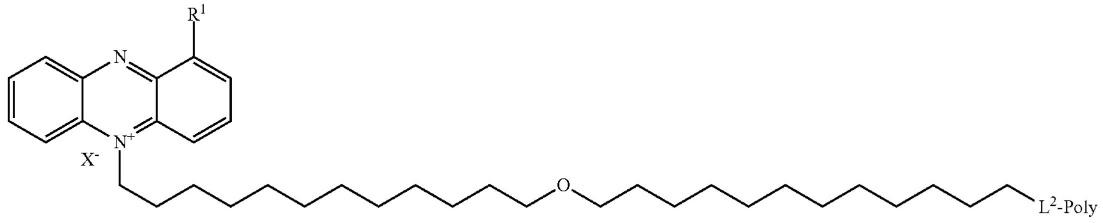
[Formula 24-2]
(B6)
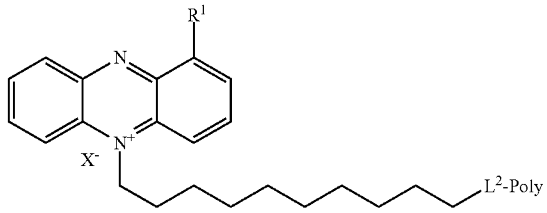
(B7)
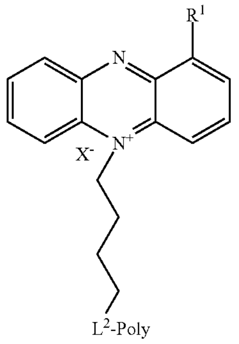
(B8)
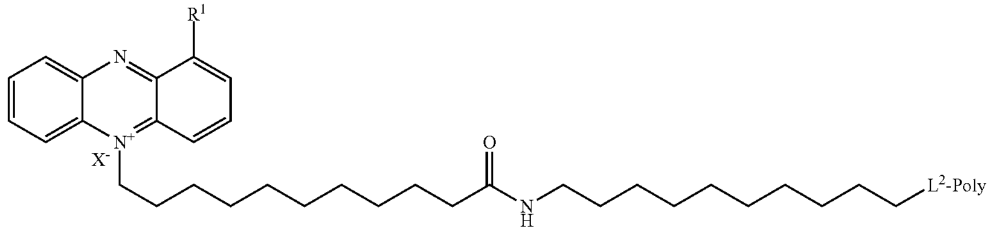
(B9)
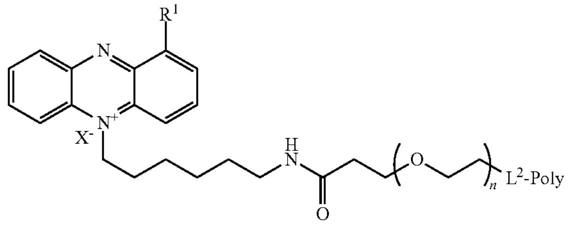

-continued
[Formula 24-3]
(2)
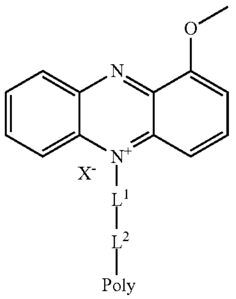
(3)
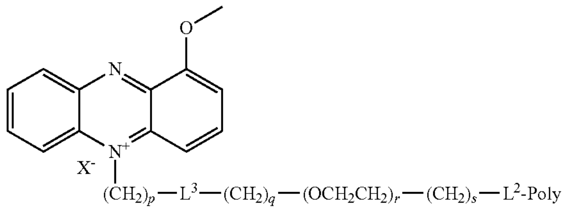
(4)
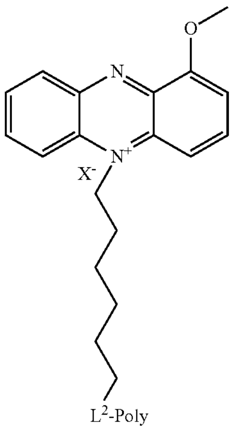
(5)
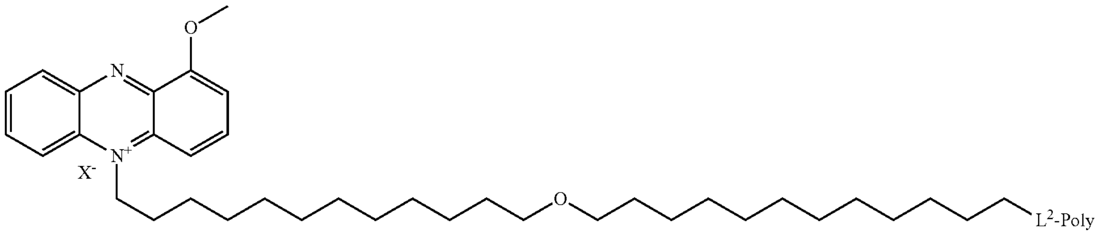
[Formula 24-4]
(6)
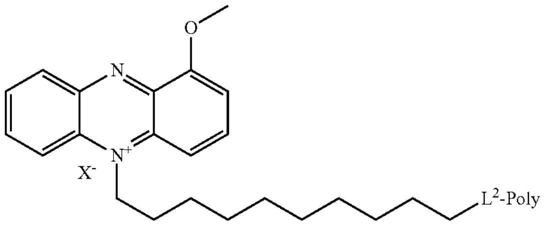
(7)
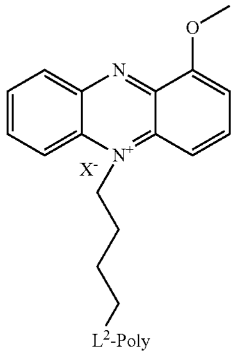

-continued (8)

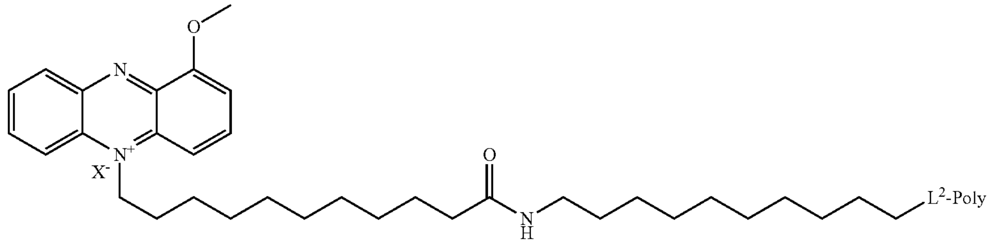

(9)

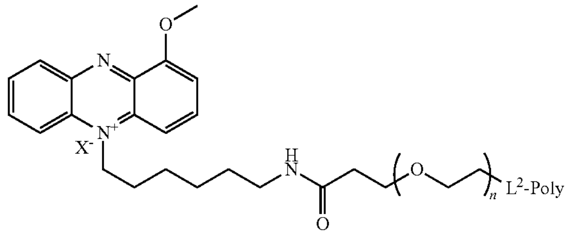

The high molecular weight polymer in the present disclosure is bonded to a redox mediator (a phenazine derivative) to prevent or suppress the leaching of the redox mediator out of a protective film. Therefore, a polymer having a molecular weight (weight-average molecular weight) above a specific level, specifically, a polymer having a weight-average molecular weight of usually 10,000 or higher, preferably 50,000 or higher, more preferably 100,000 or higher is used as a high molecular weight polymer. The weight-average molecular weight of this high molecular weight polymer is usually lower than 10,000,000, preferably lower than 1,000,000. The molecular weight (weight-average molecular weight) and the molecular weight distribution of the high molecular weight polymer can be measured by known means depending on the type of the high molecular weight polymer. For example, gel permeation chromatography (GPC), SDS-polyacrylamide gel electrophoresis (SDS-PAGE) if the high molecular weight polymer is a protein, or the like can be used. Further, if a commercially available high molecular weight polymer is purchased and used, the numerical values shown as catalog values or the like can be deemed as molecular weight (weight-average molecular weight) or the like.

The high molecular weight polymer may be any of a homopolymer, a copolymer, and a polymer obtained by binding and/or mixing these, or may be either a random polymer or a block polymer.

High molecular weight polymers are not particularly limited as long as they have a structure that can be bonded to a phenazine derivative, that is, a redox mediator (a phenazine compound, in particular, a nitrogen atom at the 5-position thereof) via a linker and can form a reagent layer containing the redox mediator on the working electrode. Examples of high molecular weight polymers include high molecular weight polymers in which a main chain is constituted by at least one atom selected from the group consisting of a carbon atom, a nitrogen atom, an oxygen atom, and a sulfur atom in which a plurality of the atoms bonds in a chain. Representative examples thereof include high molecular weight polymers in which the bonds between atoms constituting the main chain include at least one selected from the group consisting of a carbon-carbon bond, an amide bond, and an ether bond. The high molecular weight polymers may have a side chain bonded to such a main chain as described above. It is sufficient that the main chain (a terminal portion in a longitudinal direction) and/or the side chain of the high molecular weight polymer can be linked to at least one phenazine derivative. A representative example of a carbon-carbon bond is a bond derived from an ethylene carbon-carbon double bond contained in an ethylene-based polymer. A representative example of an amide bond is a bond contained in a polyamino acid-based polymer (a peptide bond) described later.

In a preferred embodiment, a high molecular weight polymer is linked to a plurality of (a large number of) phenazine derivatives in side chains. A preferred example is a high molecular weight polymer having a plurality of (a large number of) second' linkers that have a first reactive group and a second reactive group listed in the Table 1 described above as side chains and can form covalent bonds by reacting with first' linkers of the phenazine derivatives. The first reactive group or the second reactive group may be positioned, for example, at the end of a second' linker constituted by a relatively large number of atoms introduced by an addition reaction to the main chain, or may be directly bonded to the main chain or positioned at the end of a second' linker constituted by a relatively small number of atoms if a monomer used to form the main chain has the first reactive group or the second reactive group originally.

Specific examples of the high molecular weight polymer in the present disclosure include polyamino acid-based polymers (e.g., poly(L-sodium glutamate), poly(L-lysine)), polyimine-based polymers (e.g., poly(ethylenimine)), and ethylene-based polymers (e.g., polyallylamine hydrochloride, allylamine hydrochloride-diallylamine hydrochloride copolymer, allylamine-diallyldimethylammonium chloride copolymer) which have the first reactive group or the second reactive group in a side chain or the like. Of note, ethylene-based polymers include homopolymers and copolymers made of monomers containing an "ethylene carbon-carbon double bond" that can allow radical polymerization, for example, a vinyl group ($CH_2$=$CH^-$), an allyl group ($CH_2$═CH—$CH_2$—), an acryloyl group ($CH_2$═CH—C(O)—), a methacryloyl group ($CH_2$═C($CH_3$)—C(O)—), or the like (one or more types of monomers selected from these monomers), and modifiers thereof (e.g., a monomer converted from a unit derived from vinyl acetate to a vinyl alcohol by saponification, a monomer treated to impart hydrophilicity). Examples of the monomer containing an ethylene carbon-carbon double bond include ethylene, propylene, butadiene, isobutene, tetrafluoroethylene, vinyl alcohol, vinyl acetate, vinyl chloride, vinylidene chloride, styrene, methyl styrene, allylamine, diallylamine, diallyldimethylammonium chloride, acrylic acid, methacrylic acid, methyl acrylate, methyl methacrylate, and acrylonitrile. In addition, various high molecular weight polymers commonly known as biocompatible polymers, for example, polyester polymers such as polyethylene terephthalate can be used.

The high molecular weight polymer may be a protein or a polypeptide having a natural amino acid sequence or a modified (substituted, deleted, added, or the like) amino acid sequence, which is regarded as a polymer composed of amino acids as monomers (however, distinguished from the polyamino acid as a concept). Examples of such a protein include BSA and the like, which are known and commonly used as blocking agents, and oxidoreductases in the present disclosure such as glucose dehydrogenase and glucose oxidase. Further, the high molecular weight polymer may be a polynucleotide having a natural nucleotide sequence or a modified (substituted, deleted, added, or the like) nucleotide sequence, which is regarded as a polymer composed of nucleotides as monomers linked via a phosphate group.

The high molecular weight polymer is preferably hydrophilic. While the high molecular weight redox polymer needs to be hydrophilic as described above, the high molecular weight polymer does not necessarily need to be hydrophilic. This is because a high molecular weight redox polymer that is hydrophilic as a whole can be generated from a high molecular weight polymer that is not hydrophilic by bonding the high molecular weight polymer to a hydrophilic phenazine derivative. However, given that a high molecular weight polymer and a phenazine derivative are bonded (e.g., allowing a first reactive group and a second reactive group to react) typically in water containing a phenazine derivative dissolved therein or a reaction solvent containing a polar solvent, the high molecular weight polymer is preferably hydrophilic.

The high molecular weight redox polymer according to the present disclosure can be manufactured using the state of art technology of those skilled in the art. In general, a high molecular weight redox polymer can be obtained by allowing a phenazine derivative and a high molecular weight polymer separately synthesized beforehand to react according to the intended high molecular weight redox polymer.

A phenazine derivative can be obtained by allowing a selected phenazine compound and a compound that can constitute a linker having desired reactive groups (e.g., N-alkylating agent) to react under suitable conditions (temperature, time, aids, and the like) to introduce a linker (a first' linker) at a nitrogen atom at the 5-position of the phenazine compound.

A high molecular weight polymer having desired reactive groups can be obtained by polymerizing a selected monomer by an appropriate method (reaction, conditions, aids, and the like) or synthesizing as a protein or a nucleic acid.

An intended high molecular weight redox polymer can be obtained by allowing a phenazine derivative and a high molecular weight polymer to react under suitable conditions according to their respective reactive groups (a first reactive group and a second reactive group listed in Table 1). The obtained high molecular weight redox polymer may be purified by gel filtration chromatography, ultrafiltration, or the like, as necessary.

As the high molecular weight redox polymers according to the present disclosure represented by general formulas (A1) to (A9), (B1) to (B9), (1) to (9), and the like, any one type thereof may be used solely, or two or more types thereof may be used in combination as a mixture, for example. In an embodiment of the present invention, a high molecular weight redox polymer mixture containing a plurality of types of high molecular weight redox polymers of the present disclosure (e.g., high molecular weight redox polymers containing different types of high molecular weight polymers, high molecular weight redox polymers containing different types of linkers, high molecular weight redox polymers containing different types of phenazine compounds (e.g., position, number, type of a substituent)) can be provided.

—Biosensor—

The biosensor of the present disclosure for detecting or quantifying an analyte is essentially embedded and has a working electrode, a counter electrode, a reagent layer disposed on the working electrode, and a protective film covering at least the reagent layer; and the reagent layer contains an oxidoreductase that oxidizes or dehydrogenates the analyte and the high molecular weight redox polymer according to the present disclosure or a mixture thereof, representatively a high molecular weight redox polymer represented by general formula (A1):

wherein the meaning of each symbol in general formula (A1) is as described above;

or a mixture containing a plurality of types of the high molecular weight redox polymers represented by general formula (A1).

[Formula 25]

(A1)

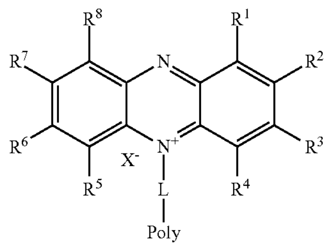

Details of the high molecular weight redox polymer contained in the reagent layer of the biosensor (examples of more specific embodiments and preferred embodiments are general formula (A2) to (A9), (B1) to (B9), and (1) to (9)) are as described above. The reagent layer of the biosensor may contain any one type of a high molecular weight redox polymer solely, or two or more types of high molecular weight redox polymers that are in a mixed or multi-layered condition or the like (for example, as a high molecular weight redox polymer mixture).

The biosensor of the present disclosure can further contain a reference electrode.

In the present disclosure, the "oxidoreductase" refers to an enzyme that can oxidize or dehydrogenate an analyte. This oxidoreductase is preferably a coenzyme-binding enzyme.

In the present disclosure, when the analyte is glucose, the oxidoreductase is a glucose oxidizing enzyme (glucose oxidase) or glucose dehydrogenase (GDH). Examples of such coenzyme-binding glucose dehydrogenases include pyrroloquinoline quinone (PQQ)-dependent GDH and flavin adenine nucleotide (FAD)-dependent GDH. Further, given the effect of maltose in a living body, GDH preferably has an enzyme activity against maltose of 5% or lower when the enzyme activity against glucose is assumed as 100%. More preferably, the enzyme activity against maltose is 3% or lower. Examples of an enzyme having such an enzyme activity include FAD-dependent GDH. Examples of such FAD-dependent GDH include those derived from the genus *Aspergillus* (e.g., *Aspergillus oryzae, Aspergillus terreus*) and the genus Mucor (refer to WO 2004/058958, JP 2008-228740, and WO 2010/140431, for example).

Further, the oxidoreductase of the present disclosure can be crosslinked with a high molecular weight redox polymer using a crosslinking agent such as glutaraldehyde, for example. Leaching of a redox mediator out of a protective film can be suppressed better because the molecular weight is increased by bonding the oxidoreductase and the high molecular weight redox polymer. However, even when the oxidoreductase and the high molecular weight redox polymer are crosslinked, the oxidoreductase needs to maintain such an activity that can measure an analyte. If the oxidoreductase is not crosslinked with a high molecular weight redox polymer, it is sufficient that the oxidoreductase is contained in the reagent layer in a state of a mixture with a high molecular weight redox polymer.

In the present disclosure, the "protective film" prevents or suppresses leaching of a substance contained in the reagent layer (mainly, a redox mediator) out of the protective film and has a pore for allowing an analyte existing outside the protective film to permeate into the protective film. Additionally, the protective film needs to be disposed on a probe, so that the protective film can cover at least the reagent layer.

Because a probe with a reagent layer formed therein which is provided in the embedded biosensor is inserted into a living body for use, the protective film covering the surface of the probe preferably has biocompatibility, such that proteins or cells are not or hardly adsorbed. In general, the protective film is preferably formed with a polymer having such a property. Examples of a polymer that can form such a protective film include a copolymer of methyl methacrylate and hydroxyethyl methacrylate, a copolymer of butyl methacrylate and hydroxyethyl methacrylate, and poly(2-methacryloyloxyethylphosphorylcholine-co-n-butyl methacrylate). Of note, a (meth)acrylate compound having a main chain similar to these polymers mentioned as examples and reactive groups that can react with a linker (first reactive groups or second reactive groups listed in Table 1) in a side chain can also be used as an "ethylene-based polymer" having a methacryloyl group or an acryloyl group mentioned as a specific example of the high molecular weight polymer.

An example of the internal structure of a probe of an embedded biosensor using the high molecular weight redox polymer of the present disclosure is shown in FIGS. 3 to 6. The structure shown in FIGS. 3 to 6 is exemplary and does not limit the scope of application of the high molecular weight redox polymer of the present disclosure to the probe.

As shown in FIG. 2, an embedded biosensor 1 comprises a main body 10 and a probe 11. FIG. 3 shows a top view of the probe 11 from the front side. The term "front side" used herein refers to the face on the side having a working electrode and a reference electrode described later. As shown in FIG. 3, in brief, the probe 11 consists of a sensing portion 121 inserted into the living body and a terminal portion 122 to be electrically connected to the internal circuit of the biosensor main body 10. The sensing portion 121 is formed thinly so as to be inserted into the body. Given that the sensing portion is inserted into the body, it is preferable generally that the length in the longitudinal direction is 20 to 3 mm (preferably 10 to 3 mm), and that the length in the short direction is 1 mm to 50 μm (preferably 500 μm to 50 μm).

A more specific structure of the probe 11 is explained using FIG. 4. FIG. 4 shows a cross-sectional view of the probe 11 by a cutting plane line A-A' in FIG. 3.

First, a conductive thin film 112 is formed by depositing carbon or a conductive metal material selected from the group consisting of metals such as gold, silver, platinum, and palladium on both sides of the insulating substrate 111 by sputtering, vapor deposition, ion plating, or the like to form a thin metal film. Then, a groove 113 of a depth to reach the surface of the insulating substrate 111 is formed by laser lithography in the conductive thin film 112 formed on one face (the front side) of the insulating substrate 111 to separate and electrically insulate a working electrode region 112*a* and a reference electrode region 112*b*.

Next, insulating resist films 116*a*, 116*b* having an opening (an opening for the reference electrode) at a prespecified position in the reference electrode region 112*b* are formed on both faces of the insulating substrate 111. However, as understood from FIG. 4, the insulating resist films 116*a*, 116*b* are not formed on the portion within a specified distance from the end of the sensing portion 112. This region on the terminal side of the working electrode region 112*a*, in which the insulating resist film is not formed, serves as a working electrode 114, and the region on the opposite side (the back side mentioned herein), in which the insulating resist film is not formed, serves as a counter electrode 117. The reference electrode 115 is formed by depositing Ag/AgCl at an opening for the reference electrode of the insulating resist film 116*a* formed on the front side of the insulating substrate 111 by a screen printing method or an ink jet printing method. Of note, a probe with three electrodes comprising a working electrode, a counter electrode, and reference electrode is shown here as an example, but a probe may have two electrodes comprising a working electrode and a counter electrode.

The reagent layer 118 contains a high molecular weight redox polymer in which at least a high molecular weight polymer and a redox mediator are bonded and an oxidoreductase and is formed on the working electrode 114. For example, the reagent layer 118 is formed by applying a solution containing a high molecular weight redox polymer and an oxidoreductase of an analyte (e.g., glucose) to the working electrode 114 and drying the solution. Of note, the reagent layer 118 can contain other components, such as conductive particles such as carbon particles and components of a buffer solution. In this case, for example, a reagent layer 118 can be formed by further adding other components to a solution containing a high molecular weight redox polymer and an oxidoreductase and applying and drying the solution. In the high molecular weight redox polymer, an oxidoreductase of an analyte may be bonded to a redox mediator as a high molecular weight polymer (a protein). Additionally, the high molecular weight redox polymer (a high molecular weight polymer contained therein is not an oxidoreductase of an analyte) may be crosslinked with an oxidoreductase of an analyte. In these cases, it is sufficient that the reagent layer 118 contains at least a high molecular weight redox polymer, and the reagent layer 118 does not need to further contain an oxidoreductase separately.

Finally, a protective film 119 can be formed on both faces and side faces and at ends of the sensing portion 121 by immersing the sensing portion 121 in a solution containing a polymer for the protective film and drying the solution, and this sensing portion can be used as a probe 11 of a biosensor.

FIG. 5 shows a cross-sectional view by a cutting plane line B-B' in FIG. 4, and FIG. 6 shows a cross-sectional view by a cutting plane line C-C' in FIG. 4. FIG. 5 shows, from the front side towards the back side (in the direction of the arrow in the figure), a protective film 119, a reagent layer 118, a working electrode 114, an insulating substrate 111, a counter electrode 117, and a protective film 119. FIG. 6 shows, from the front side towards the back side (in the direction of the arrow in the figure), a protective film 119, a reference electrode 115 (an insulating resist film 116*a*), a working electrode region 112*a*, an insulating substrate 111, a counter electrode region 112*c*, an insulating resist film 116*b*, and a protective film 119. Of note, the working electrode region 112*a* and the counter electrode region 112*c* shown in FIG. 6 do not function as a working electrode and a counter electrode because these regions have the insulating resist films 116*a*, 116*b on the upper surface thereof.*

EXAMPLES

Examples of the embodiments of the high molecular weight redox polymer and the biosensor of the present disclosure are explained more specifically below through examples (including synthesis examples, a comparative example, and evaluation tests). These examples, as the embodiments of the present invention, use phenazine derivatives represented by general formulas (1) to (9), but it is construed that the present invention can be implemented similarly by using other compounds in general that fall within the scope of general formula (A1) of the present invention.

It should be noted that the general formulas of the high molecular weight redox polymers and the high molecular weight polymers used for manufacture thereof, which are shown in the examples, are expressed to indicate that a phenazine derivative is bonded to all repeating units derived from each monomer (a structure surrounded by parentheses) constituting a high molecular weight polymer. However, this expression is a measure for convenience, and phenazine derivatives in actual high molecular weight redox polymers do not necessarily need to bind to all repeating units derived from each monomer constituting a high molecular weight polymer depending on the reaction conditions at the time of manufacture. The results of the "evaluation tests" demonstrate that various high molecular weight redox polymers manufactured in the examples can implement the invention according to the present disclosure.

Example 1

Manufacture of PGA-C24-Ph 6.47 mg of 5-{12-[(12-ammoniododecyl)oxy]dodecyl}-1-methoxyphenazin-5-ium dinitrate (Ph-C24-NH3+) (Tokyo Kasei Kogyo Co., Ltd.) was weighed as a phenazine derivative and dissolved in 500 μL of ethanol.

Meanwhile, 11.86 mg of poly(L-sodium glutamate) (Peptide Institute, Inc.; Code 3063; M.W.>12,000, cutoff of by dialysis) represented by general formula (11a) was weighed as a high molecular weight polymer which is a polyamino acid-based polymer and dissolved in 1.5 mL of 100 mM 2-morpholinoethanesulfonic acid (MES) buffer solution (pH 6.0). Separately, 8.8 mg of water-soluble carbodiimide (WSC) (Dojindo Laboratories) was weighed and dissolved in 500 μL of 100 mM MES buffer solution (pH 6.0). The above-described three solutions were mixed, and the mixture was allowed to react with stirring at room temperature for 4 hours.

[Formula 26]

(11a)

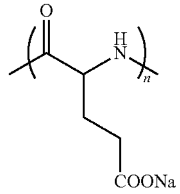

The reaction solution was subjected to gel filtration chromatography using PD-10 Column (GE Healthcare) with phosphate buffered saline (PBS, pH 7.4) as an elution buffer. After gel filtration, the solution was ultrafiltered using a centrifugal ultrafiltration filter (Amicon Ultra-4 10k; Merck Millipore). A high molecular weight redox polymer (PGA-C24-Ph) represented by general formula (5a) in which phenazine was covalently bonded to poly(L-sodium glutamate) was obtained by the above-described procedure.

[Formula 27]

(5a)

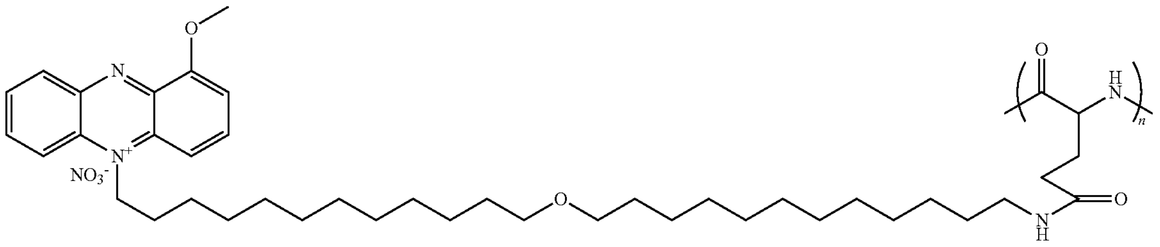

A solution of the obtained PGA-C24-Ph was diluted 20-fold, and the absorbance at 386 nm was measured for the diluted solution using a microplate (Greiner Bio-One UV-STAR MICROPALLETE 96 WELL F-BODEN) and a plate reader (TECAN; Infinite M200 PRO). The concentration of the solution of PGA-C24-Ph was adjusted with PBS to have an absorbance of approximately 0.55 at 386 nm when the solution of PGA-C24-Ph was diluted 20-fold. The absorbance peak appearing at 386 nm results from the phenazine derivative (the maximum peak resulting from a phenazine derivative appears generally at 384 to 386 nm). The absorbance was obtained by reducing the measured absorbance of PBS as a blank value.

Example 2

Manufacture of PLL-C11-Ph 0.70 mg of 5-{11-[(2,5-dioxopyrrolidin-1-yl)oxy]-11-oxoundecyl}-1-methoxyphenazin-5-ium nitrate (Ph-C11-Su) (Tokyo Kasei Kogyo Co., Ltd.) was weighed as a phenazine derivative and dissolved in 500 μL of 100 mM 2-morpholinoethanesulfonic acid (MES) buffer solution (pH 6.0). Meanwhile, 3.34 mg of poly(L-lysine) hydrochloride (Peptide Institute, Inc.; Code 3075; M.W.>12,000, cutoff of by dialysis) represented by general formula (11b) was weighed as a high molecular weight polymer which is a polyamino acid-based polymer and dissolved in 500 μL of 100 mM MES buffer solution (pH 6.0). The above-described two solutions were mixed, and the mixture was allowed to react with stirring at room temperature for 4 hours.

[Formula 28]

(11b)

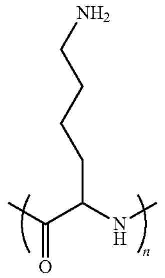

The reaction solution was subjected to gel filtration chromatography using PD-10 Column (GE Healthcare) with PBS as an elution buffer. After gel filtration, the solution was ultrafiltered using a centrifugal ultrafiltration filter (Amicon Ultra-4 30k; Merck Millipore).

A high molecular weight redox polymer (PLL-C11-Ph) represented by general formula (8a) in which phenazine was covalently bonded to poly(L-lysine) hydrochloride was obtained by the above-described procedure.

[Formula 29]

(8a)

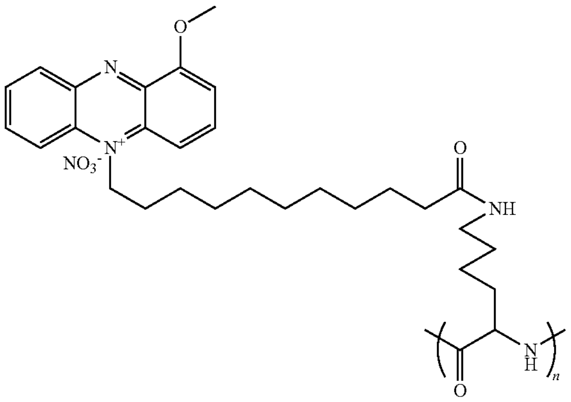

A solution of the obtained PLL-C11-Ph was diluted 20-fold, and the absorbance at 386 nm was measured for the diluted solution using a microplate (Greiner Bio-One UV-STAR MICROPALLETE 96 WELL F-BODEN) and a plate reader (TECAN; Infinite M200 PRO). The concentration of the solution of PLL-C11-Ph was adjusted with PBS to have an absorbance of approximately 0.55 at 386 nm when the solution of GDH-05-Ph was diluted 20-fold. The absorbance was obtained by reducing the measured absorbance of PBS as a blank value.

Example 3

Manufacture of PLL-05-Ph 1

0.6 mg of 5-{[(2,5-dioxopyridin-1-yl)oxy]-5-oxopentyl}-1-methoxyphenazinium nitrate (Ph-05-Su) (Tokyo Kasei Kogyo Co., Ltd.) was weighed as a phenazine derivative and dissolved in 120 μL of 100 mM 2-morpholinoethanesulfonic acid (MES) buffer solution (pH 6.0). Meanwhile, 5 mg of the same poly(L-lysine) hydrochloride (Peptide Institute, Inc.; Code 3075; M.W. >12,000, cutoff of by dialysis) as in Example 2 was weighed as a high molecular weight polymer and dissolved in 1 mL of 100 mM MES buffer solution (pH 6.0). The above-described two solutions were mixed, and the mixture was allowed to react with stirring at room temperature for 4 hours.

The reaction solution was subjected to gel filtration chromatography using PD-10 Column (GE Healthcare) with PBS as an elution buffer. After gel filtration, the solution was ultrafiltered using a centrifugal ultrafiltration filter (Amicon Ultra-4 30k; Merck Millipore).

A high molecular weight redox polymer (PLL-05-Ph 1) represented by general formula (8b) in which phenazine was covalently bonded to poly(L-lysine) hydrochloride was obtained by the above-described procedure.

[Formula 30]

(8b)

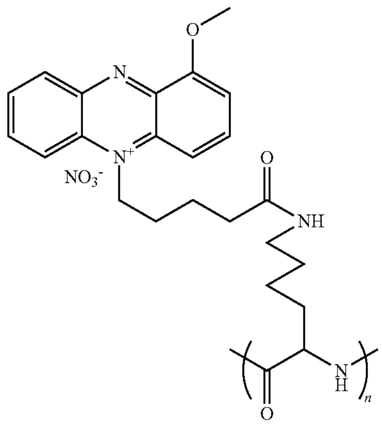

A solution of the obtained PLL-05-Ph_1 was diluted 20-fold, and the absorbance at 386 nm was measured for the diluted solution using a microplate (Greiner Bio-One UV-STAR MICROPALLETE 96 WELL F-BODEN) and a plate reader (TECAN; Infinite M200 PRO). The concentration of the solution of PLL-05-Ph_1 was adjusted with PBS to have an absorbance of approximately 0.55 at 386 nm when the solution of PLL-05-Ph_1 was diluted 20-fold. The absorbance was obtained by reducing the measured absorbance of PBS as a blank value.

Example 4

Manufacture of PAA-05-Ph 2 mg of Ph-05-Su (Tokyo Kasei Kogyo Co., Ltd.) was weighed as a phenazine derivative and dissolved in 500 μL of 100 mM 2-morpholinoethanesulfonic acid (MES) buffer solution (pH 6.0). Meanwhile, 3.31 mg of polyallylamine hydrochloride (Sigma-Aldrich; Product Number 283215; weight-average molecular weight (PEG equivalent) by GPC measurement Mw 17,500) represented by general formula (11c) was weighed as a high molecular weight polymer which is an ethylene-based polymer and dissolved in 500 μL of 100 mM MES buffer solution (pH 6.0). The above-described two solutions were mixed, and the mixture was allowed to react with stirring at room temperature for 4 hours.

[Formula 31]

(11c)

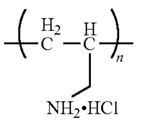

The reaction solution was subjected to gel filtration chromatography using PD-10 Column (GE Healthcare) with 10 mM sodium phosphate buffer solution (pH 6.5) as an elution buffer. After gel filtration, the solution was ultrafiltered using a centrifugal ultrafiltration filter (Amicon Ultra-4 10k; Merck Millipore).

A high molecular weight redox polymer (PAA-05-Ph) represented by general formula (8c) in which phenazine was covalently bonded to polyallylamine hydrochloride was obtained by the above-described procedure.

[Formula 32]

(8c)

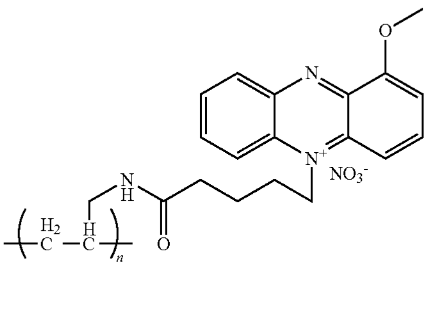

A solution of the obtained PAA-05-Ph was diluted 20-fold, and the absorbance at 386 nm was measured for the diluted solution using a microplate (Greiner Bio-One UV-STAR MICROPALLETE 96 WELL F-BODEN) and a plate reader (TECAN; Infinite M200 PRO). The concentration of the solution of PAA-05-Ph was adjusted with PBS to have an absorbance of approximately 0.55 at 386 nm when the solution of PAA-05-Ph was diluted 20-fold. The absorbance was obtained by reducing the measured absorbance of 10 mM sodium phosphate buffer solution (pH 6.5) as a blank value.

Example 5: Manufacture of PEI-C5-Ph 2.38 mg of 5-{[(2,5-dioxopyridin-1-yl)oxy]-5-oxopentyl}-1-methoxyphenazinium nitrate (Ph-C5-Su) (Tokyo Kasei Kogyo Co., Ltd.) was weighed as a phenazine derivative and dissolved in 1 mL of 100 mM 2-morpholinoethanesulfonic acid (MES) buffer solution (pH 6.0). Meanwhile, 5 mg of poly(ethylenimine) solution (Sigma-Aldrich; Product Number 181978; number-average molecular weight by GPC measurement Mn ≈60,000; weight-average molecular weight by LS measurement Mw ≈750,000; 50% by weight in $H_2O$) represented by general formula (IId) was weighed as a high molecular weight polymer which is a polyimine-based polymer and dissolved in 1.5 mL of 100 mM MES buffer solution (pH 6.0). The above-described two solutions were mixed, and the mixture was allowed to react with stirring at room temperature for 4 hours.

[Formula 33]

(11d)

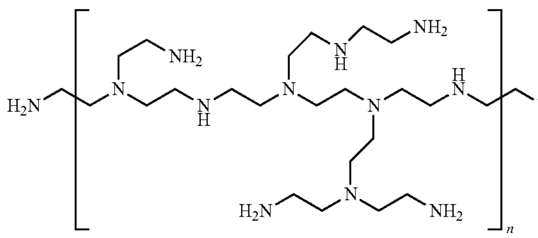

The reaction solution was subjected to gel filtration chromatography using PD-10 Column (GE Healthcare) with PBS as an elution buffer. After gel filtration, the solution was ultrafiltered using a centrifugal ultrafiltration filter (Amicon Ultra-4 30k; Merck Millipore).

A high molecular weight redox polymer (PEI-05-Ph) represented by general formula (8d) in which phenazine was covalently bonded to polyethylenimine was obtained by the above-described procedure.

[Formula 34]

(8d)

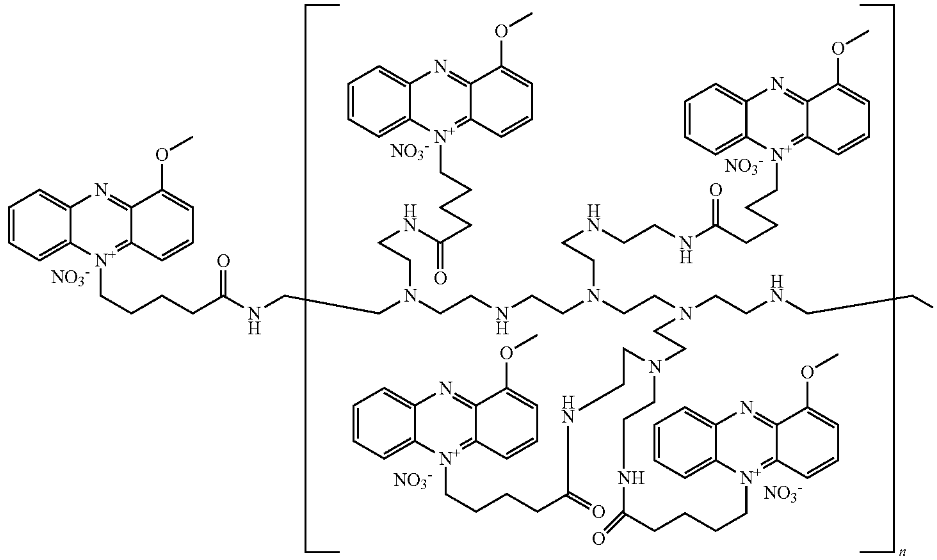

A solution of the obtained PEI-05-Ph was diluted 20-fold, and the absorbance at 386 nm was measured for the diluted solution using a microplate (Greiner Bio-One UV-STAR MICROPALLETE 96 WELL F-BODEN) and a plate reader (TECAN; Infinite M200 PRO). The concentration of the solution of PEI-05-Ph was adjusted with PBS to have an absorbance of approximately 0.55 at 386 nm when the solution of PEI-05-Ph was diluted 20-fold. The absorbance was obtained by reducing the measured absorbance of PBS as a blank value.

Example 6

Manufacture of PAA-DAA-05-Ph 0.91 mg of Ph-05-Su (Tokyo Kasei Kogyo Co., Ltd.) was weighed as a phenazine derivative and dissolved in 1 mL of 100 mM 2-morpholinoethanesulfonic acid (MES) buffer solution (pH 6.0). Meanwhile, 8.75 mg of an aqueous solution of allylamine hydrochloride-diallylamine hydrochloride copolymer (Nittobo Medical Co., Ltd.; PAA-Dll-HCL; weight-average molecular weight Mw =100,000; concentration 40%; pH (5% sol) 2-3; viscosity 600 mPa s) represented by general formula (11e) was weighed as a high molecular weight polymer which is an ethylene-based polymer (copolymer) and dissolved in 1.5 mL of 100 mM MES buffer solution (pH 6.0). The above-described two solutions were mixed, and the mixture was allowed to react with stirring at room temperature for 4 hours.

[Formula 35]

(11e)

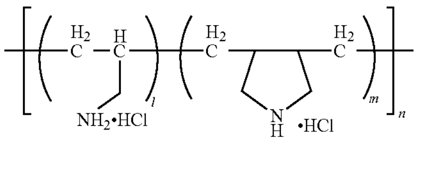

The reaction solution was subjected to gel filtration chromatography using PD-10 Column (GE Healthcare) with PBS as an elution buffer. After gel filtration, the solution was ultrafiltered using a centrifugal ultrafiltration filter (Amicon Ultra-4 30k; Merck Millipore).

A high molecular weight redox polymer (PAA-DAA-05-Ph) represented by general formula (8e) in which phenazine was covalently bonded to allylamine hydrochloride-diallylamine hydrochloride copolymer was obtained by the above-described procedure.

[Formula 36]

(8e)

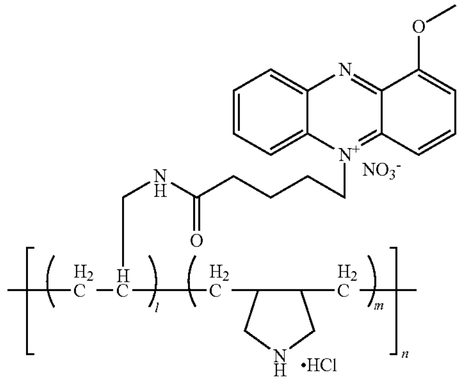

A solution of the obtained PAA-DAA-05-Ph was diluted 20-fold, and the absorbance at 386 nm was measured for the diluted solution using a microplate (Greiner Bio-One UV-STAR MICROPALLETE 96 WELL F-BODEN) and a plate reader (TECAN; Infinite M200 PRO). The concentration of the solution of PAA-DAA-05-Ph was adjusted with PBS to have an absorbance of approximately 0.55 at 386 nm when the solution of PAA-DAA-05-Ph was diluted 20-fold. The absorbance was obtained by reducing the measured absorbance of PBS as a blank value.

Example 7

Manufacture of PAA-DADMA-05-Ph 2.04 mg of Ph-05-Su (Tokyo Kasei Kogyo Co., Ltd.) was weighed as a phenazine derivative and dissolved in 1 mL of 100 mM 2-morpholinoethanesulfonic acid (MES) buffer solution (pH 6.0). Meanwhile, 6.88 mg of an aqueous solution of allylamine-diallyldimethylammonium chloride copolymer (Nittobo Medical Co., Ltd.; PAA-1123; weight-average molecular weight Mw =18,000; concentration 15%; pH (5% sol) 11; viscosity 14 mPa s) represented by general formula (11f) was weighed as a high molecular weight polymer which is an ethylene-based polymer (copolymer) and dissolved in 1.5 mL of 100 mM MES buffer solution (pH 6.0). The above-described two solutions were mixed, and the mixture was allowed to react with stirring at room temperature for 4 hours.

[Formula 37]

(11f)

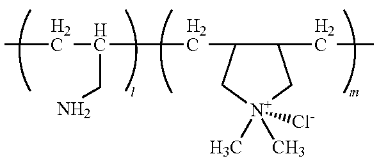

The reaction solution was subjected to gel filtration chromatography using PD-10 Column (GE Healthcare) with PBS as an elution buffer. After gel filtration, the solution was ultrafiltered using a centrifugal ultrafiltration filter (Amicon Ultra-4 10k; Merck Millipore).

A high molecular weight redox polymer (PAA-DADMA-05-Ph) represented by general formula (8f) in which phenazine was covalently bonded to an allylamine-diallyldimethylammonium chloride copolymer was obtained by the above-described procedure.

[Formula 38]

(8f)

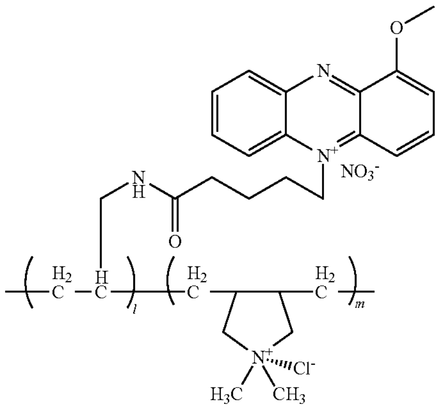

A solution of the obtained PAA-DADMA-05-Ph was diluted 20-fold, and the absorbance at 386 nm was measured for the diluted solution using a microplate (Greiner Bio-One UV-STAR MICROPALLETE 96 WELL F-BODEN) and a plate reader (TECAN; Infinite M200 PRO). When the solution of PAA-DADMA-05-Ph was diluted 20-fold, the concentration of the solution of PAA-DADMA-05-Ph was adjusted with PBS to have an absorbance of approximately 0.55 at 386 nm. The absorbance was obtained by reducing the measured absorbance of PBS as a blank value.

Example 8

Manufacture of BSA-05-Ph 0.43 mg of Ph-05-Su (Tokyo Kasei Kogyo Co., Ltd.) was weighed as a phenazine derivative and dissolved in 300 μL of 100 mM 4-(2-hydroxyethyl)-1-piperazineethanesulfonic acid (HEPES) buffer solution (pH 7.0). Meanwhile, 0.6 mg of bovine serum albumin (BSA) (Nacalai Tesque, Inc.; Product Code 01860-65; General Grade; pH 7.0) was weighted as a high molecular weight polymer which is a protein and dissolved in 200 μL of 100 mM HEPES buffer solution (pH 7.0). The above-described two solutions were mixed, and the mixture was allowed to react with stirring at room temperature for 4 hours.

The reaction solution was subjected to gel filtration chromatography using PD MiniTrap G-25 (GE Healthcare) with PBS as an elution buffer. After gel filtration, the solution was ultrafiltered using a centrifugal ultrafiltration filter (Amicon Ultra-4 30k; Merck Millipore).

A protein (BSA-05-Ph) in which phenazine was covalently bonded to an amino group in BSA was obtained as a high molecular weight redox polymer by the above-described procedure.

A solution of the obtained BSA-05-Ph was diluted 20-fold, nd the absorbance at 386 nm was measured for the diluted solution using a microplate (Greiner Bio-One UV-STAR MICROPALLETE 96 WELL F-BODEN) and a plate reader (TECAN; Infinite M200 PRO). The concentration of the solution of BSA-05-Ph was adjusted with PBS to have an absorbance of approximately 0.55 at 386 nm when the solution of BSA-05-Ph was diluted 20-fold. The absorbance was obtained by reducing the measured absorbance of PBS as a blank value.

Example 9

Manufacture of GDH-05-Ph 0.86 mg of Ph-05-Su (Tokyo Kasei Kogyo Co., Ltd.) was weighed as a phenazine derivative and dissolved in 300 μL of 100 mM HEPES buffer solution (pH 7.0). Meanwhile, 1.37 mg of glucose dehydrogenase (FAD-dependent) derived from *Aspergillus oryzae* (BBI International; GDH GLD1) was weighed as a high molecular weight polymer which is a protein and dissolved in 200 μL of 100 mM HEPES buffer solution (pH 7.0). The above-described two solutions were mixed, and the mixture was allowed to react with stirring at room temperature for 4 hours.

The reaction solution was subjected to gel filtration chromatography using PD MiniTrap G-25 (GE Healthcare) with PBS as an elution buffer. After gel filtration, the solution was ultrafiltered using a centrifugal ultrafiltration filter (Amicon Ultra-4 30k; Merck Millipore).

A protein (GDH-05-Ph) in which phenazine was covalently bonded to glucose dehydrogenase was obtained as a high molecular weight redox polymer by the above-described procedure.

A solution of the obtained GDH-C5-Ph was diluted 20-fold, and the absorbance at 386 nm was measured for the diluted solution using a microplate (Greiner Bio-One UV-STAR MICROPALLETE 96 WELL F-BODEN) and a plate reader (TECAN; Infinite M200 PRO). The concentration of the solution of GDH-C5-Ph was adjusted with PBS to have an absorbance of approximately 0.55 at 386 nm when the solution of GDH-C5-Ph was diluted 20-fold. The absorbance was obtained by reducing the measured absorbance of PBS as a blank value.

Example 10

Manufacture of GDH-C22-Ph 2.78 mg of 5-{11-[11-(2,5-dioxopyrrolidin-1-yloxy)-11-oxoundecylamino]-11-oxoundecyl}-1-methoxyphenazin-5-ium nitrate (Ph-C22-Su) (Tokyo Kasei Kogyo Co., Ltd.) was weighed as a phenazine derivative and dissolved in 500 μL of ethanol. Meanwhile, 15 mg of glucose dehydrogenase (FAD-dependent) (BBI International; GDH GLD1) was weighed as a high molecular weight polymer which is a protein and dissolved in 2 mL of 100 mM HEPES buffer solution (pH 7.0). The above-described two solutions were mixed, and the mixture was allowed to react with stirring at room temperature for 4 hours.

The reaction solution was subjected to gel filtration chromatography using PD-10 (GE Healthcare) with PBS as an elution buffer. After gel filtration, the solution was ultrafiltered using a centrifugal ultrafiltration filter (Amicon Ultra-4 30k; Merck Millipore).

A protein (GDH-C22-Ph) in which phenazine was covalently bonded to an amino group of glucose dehydrogenase was obtained as a high molecular weight redox polymer by the above-described procedure.

A solution of the obtained GDH-C22-Ph was diluted 20-fold, and the absorbance at 386 nm was measured for the diluted solution using a microplate (Greiner Bio-One UV-STAR MICROPALLETE 96 WELL F-BODEN) and a plate reader (TECAN; Infinite M200 PRO). The concentration of the solution of GDH-C22-Ph was adjusted with PBS to have an absorbance of approximately 0.55 at 386 nm when the solution of GDH-C22-Ph was diluted 20-fold. The absorbance was obtained by reducing the measured absorbance of PBS as a blank value.

Example 11

Manufacture of PLL-05-Ph 2

2 mg of Ph-05-Su (Tokyo Kasei Kogyo Co., Ltd.) was weighed as a phenazine derivative and dissolved in 500 μL of 100 mM MES buffer solution (pH 6.0). Meanwhile, 11.33 mg of poly(L-lysine) hydrochloride (Peptide Institute, Inc.; Code 3075; M.W.>12,000, cutoff of by dialysis) was weighed as a high molecular weight polymer which is a polyamino acid-based polymer and dissolved in 500 μL of 100 mM MES buffer solution (pH 6.0). The above-mentioned two solutions were mixed, and the mixture was allowed to react with stirring at room temperature for 4 hours.

The reaction solution was subjected to gel filtration chromatography using PD-10 Column (GE Healthcare) with PBS as an elution buffer. After gel filtration, the solution was ultrafiltered using a centrifugal ultrafiltration filter (Amicon Ultra-4 30k; Merck Millipore).

A high molecular weight redox polymer (PLL-05-Ph 2) generated by general formula (8 g) in which phenazine was covalently bonded to poly(L-lysine) hydrochloride was obtained by the above-described procedure.

[Formula 39]

(8g)

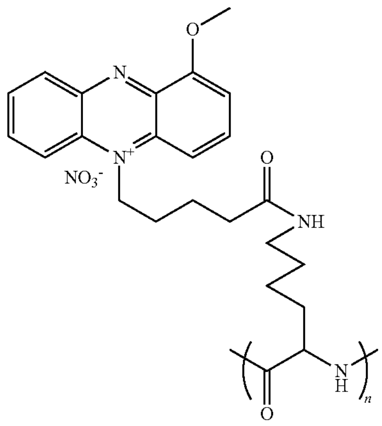

A solution of the obtained PLL-05-Ph_2 was adjusted with PBS to have an absorbance of a range of 0.52 to 0.57 at 386 nm with measuring in a microplate (Greiner Bio-One UV-STAR MICROPALLETE 96 WELL F-BODEN) using a plate reader (TECAN; Infinite M200 PRO). The absorbance was obtained by reducing the measured absorbance of PBS as a blank value.

Example 12

PLL-PEGS-Ph 2 mg of 5-(6-aminohexyl)-1-methoxyphenazinium nitrate (Ph-C6-NH2) (Tokyo Kasei Kogyo Co., Ltd.) was weighed and dissolved in 300 μL of 100 mM MES buffer solution (pH 6.0). Separately, 1.8 mg of Acid-PEGS-NHS ester (BroadPharm) was weighed and dissolved in 300 μL of 100 mM MES buffer solution (pH 6.0). The above-mentioned two solutions were mixed, and the mixture was allowed to react with stirring at room temperature for approximately 20 hours to obtain Solution A containing a PEG chain-bonded phenazinium nitrate represented by general formula (10f) as a phenazine derivative.

[Formula 40]

(10f)

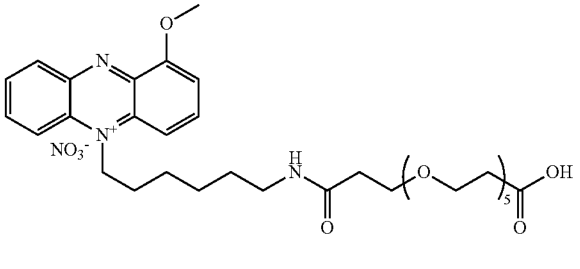

Meanwhile, 11.02 mg of poly(L-lysine) hydrochloride (Peptide Institute, Inc.; Code 3075; M.W. >12,000, cutoff of by dialysis) was weighed as a high molecular weight polymer which is a polyamino acid-based polymer and dissolved in 300 μL of 100 mM MES buffer solution (pH 6.0). Separately, 4 mg of water-soluble carbodiimide (WSC) (Dojindo Laboratories) was weighed and dissolved in 100 μL of 100 mM MES buffer solution (pH 6.0). The above-mentioned poly(L-lysine) hydrochloride and WSC solution were mixed into Solution A sequentially, and the mixture was allowed to react with stirring at room temperature for 4 hours.

The reaction solution was subjected to gel filtration chromatography using PD-10 Column (GE Healthcare) with PBS as an elution buffer. After gel filtration, the solution was ultrafiltered using a centrifugal ultrafiltration filter (Amicon Ultra-4 30k; Merck Millipore).

A high molecular weight redox polymer (PLL-PEG5-Ph) represented by general formula (9b) in which phenazine was covalently bonded to poly(L-lysine) hydrochloride grafted with a polyethylene glycol (PEG) chain comprising five units of ethylene glycol was obtained by the above-described procedure.

[Formula 41]

(9b)

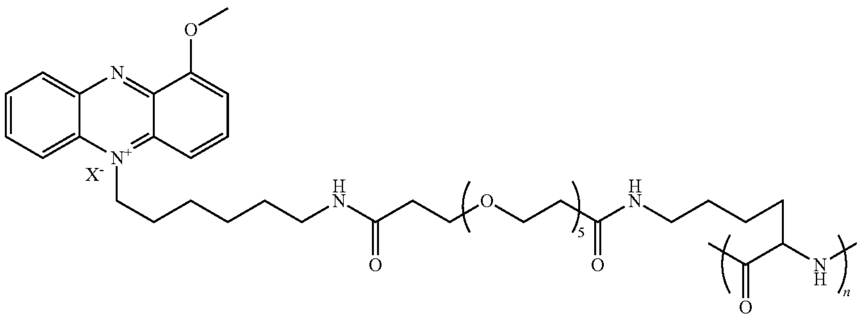

A solution of the obtained PLL-PEG5-Ph was adjusted with PBS to have an absorbance of a range of 0.52 to 0.57 at 386 nm with measuring in a microplate (Greiner Bio-One UV-STAR MICROPALLETE 96 WELL F-BODEN) using a plate reader (TECAN; Infinite M200 PRO). The absorbance was obtained by reducing the measured absorbance of PBS as a blank value.

Example 13

Manufacture of PLL-PEG13-Ph 2 mg of Ph-C6-NH2 (Tokyo Kasei Kogyo Co., Ltd.) was weighed and dissolved in 300 μL of 100 mM MES buffer solution (pH 6.0). Separately, 3.26 mg of Acid-PEG13-NHS ester (BroadPharm) was weighed and dissolved in 300 μL of 100 mM MES buffer solution (pH 6.0). The above-described two solutions were mixed, and the mixture was allowed to react with stirring at room temperature for approximately 20 hours to obtain Solution B containing PEG chain-bonded phenazinium nitrate represented by general formula (10 g) as a phenazine derivative.

[Formula 42]

(10g)

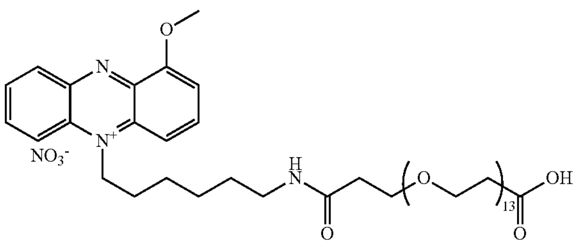

Meanwhile, 11.02 mg of poly(L-lysine) hydrochloride (Peptide Institute, Inc.; Code 3075; M.W.>12,000, cutoff of by dialysis) was weighed as a high molecular weight polymer which is a polyamino acid-based polymer and dissolved in 300 μL of 100 mM MES buffer solution (pH 6.0). Separately, 4 mg of water-soluble carbodiimide (WSC) (Dojindo Laboratories) was weighed and dissolved in 100 μL of 100 mM MES buffer solution (pH 6.0). The above-described poly(L-lysine) hydrochloride and WSC solution were mixed into Solution B sequentially, and the mixture was allowed to react with stirring at room temperature for 4 hours.

The reaction solution was subjected to gel filtration chromatography using PD-10 Column (GE Healthcare) with PBS as an elution buffer. After gel filtration, the solution was ultrafiltered using a centrifugal ultrafiltration filter (Amicon Ultra-4 30k; Merck Millipore).

A high molecular weight redox polymer (PLL-PEG13-Ph) represented by general formula (9c) in which phenazine was covalently bonded to poly(L-lysine) hydrochloride grafted with a polyethylene glycol (PEG) chain comprising 13 units of ethylene glycol was obtained by the above-described procedure.

[Formula 43]

(9c)

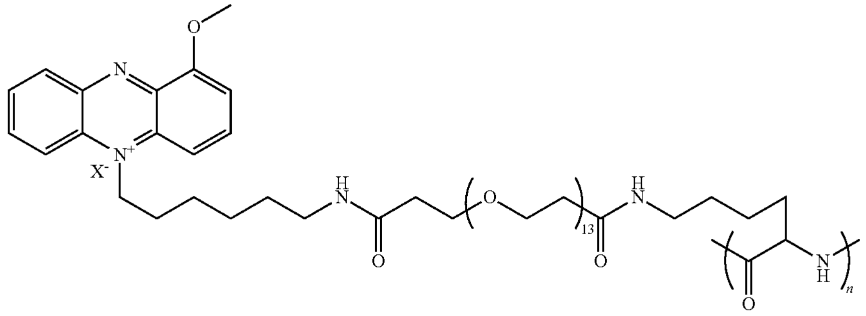

A solution of the obtained PLL-PEG13-Ph was adjusted with PBS to have an absorbance of a range of 0.52 to 0.57 at 386 nm with measuring in a microplate (Greiner Bio-One UV-STAR MICROPALLETE 96 WELL F-BODEN) using a plate reader (TECAN; Infinite M200 PRO). The absorbance was obtained by reducing the measured absorbance of PBS as a blank value.

Example 14

Manufacture of PLL-PEG25-Ph 2 mg of Ph-C6-NH2 (Tokyo Kasei Kogyo Co., Ltd.) was weighed and dissolved in 300 μL of 100 mM MES buffer solution (pH 6.0). Separately, 5.44 mg of Acid-PEG25-NHS ester (BroadPharm) was weighed and dissolved in 300 μL of 100 mM MES buffer solution (pH 6.0). The above-described two solutions were mixed, and the mixture was allowed to react with stirring at room temperature for approximately 20 hours to obtain Solution C containing PEG chain-bonded phenazinium nitrate represented by general formula (10h) as a phenazine derivative.

[Formula 44]

(10h)

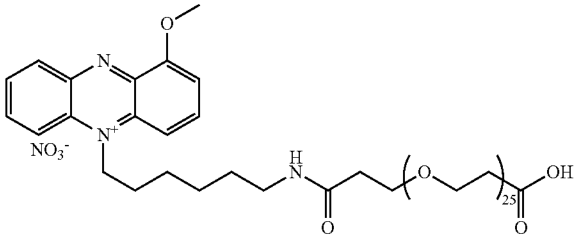

Meanwhile, 11.02 mg of poly(L-lysine) hydrochloride (Peptide Institute, Inc.; Code 3075; M.W. >12,000, cutoff of by dialysis), which is a polyamino acid-based polymer, was weighed and dissolved in 300 μL of 100 mM MES buffer solution (pH 6.0). Separately, 4 mg of water-soluble carbodiimide (WSC) (Dojindo Laboratories) was weighed and dissolved in 100 μL of 100 mM MES buffer solution (pH 6.0). The above-mentioned poly(L-lysine) hydrochloride and WSC solution were mixed into Solution C sequentially, and the mixture was allowed to react with stirring at room temperature for 4 hours.

The reaction solution was subjected to gel filtration chromatography using PD-10 Column (GE Healthcare) with PBS as an elution buffer. After gel filtration, the solution was ultrafiltered using a centrifugal ultrafiltration filter (Amicon Ultra-4 30k; Merck Millipore).

A high molecular weight redox polymer (PLL-PEG25-Ph) in which phenazine was covalently bonded to poly(L-lysine) hydrochloride grafted with polyethylene glycol (PEG) chain comprising 25 units of ethylene glycol represented by general formula (9d) was obtained by the above-described procedure.

[Formula 45]

(9c)

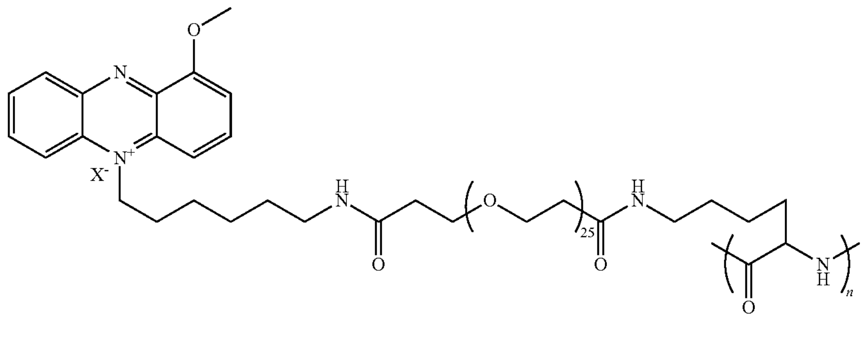

A solution of the obtained PLL-PEG25-Ph was adjusted with PBS to have an absorbance of a range of 0.52 to 0.57 at 386 nm with measuring in a microplate (Greiner Bio-One UV-STAR MICROPALLETE 96 WELL F-BODEN) using a plate reader (TECAN; Infinite M200 PRO). The absorbance was obtained by reducing the measured absorbance of PBS as a blank value.

Comparative Example 1

0.63 mg of Ph-C6-NH2 (Tokyo Kasei Kogyo Co., Ltd.) was weighed and dissolved in 500 μL of PBS to obtain a solution of Ph-C6-NH2.

The obtained solution of Ph-C6-NH2 was diluted 20-fold, and the absorbance at 386 nm was measured for the diluted solution using a microplate (Greiner Bio-One UV-STAR MICROPALLETE 96 WELL F-BODEN) and a plate reader (TECAN; Infinite M200 PRO). The concentration of the solution of Ph-C6-NH2 was adjusted with PBS to have an absorbance of approximately 0.55 at 386 nm when the solution of Ph-C6-NH2 was diluted 20-fold. The absorbance was obtained by reducing the measured absorbance of PBS as a blank value.

C. Evaluation Tests (1) Leaching of Mediators

Cyclic voltammetry was performed at a sweep rate of 10 mV/s using a potentiostat (BAS Inc.) with three electrodes comprising gold electrodes as a working electrode and a counter electrode and Ag/AgCl (saturated potassium chloride) (BAS Inc.) as a reference electrode.

The reagent layer on the working electrode was formed by any of the following (i) to (iii):

(i) 10 μL each of solutions of various phenazine derivative-bonded high molecular weight redox polymers to which the synthesized high molecular weight polymers obtained in Examples 1 to 7 were bonded was applied on the working electrode and dried.

(ii) 0.6 μL of a ketjen black suspension was applied on the working electrode and dried for approximately 10 minutes. Then, 0.6 μL each of solutions of various phenazine derivative-bonded proteins to which the proteins obtained in Examples 8 to 10 were bonded was applied and dried for approximately one hour.

(iii) 10 μL of a solution of Ph-C6-NH2 obtained in Comparative Example 1 was applied on the working electrode and dried.

Figure 7:
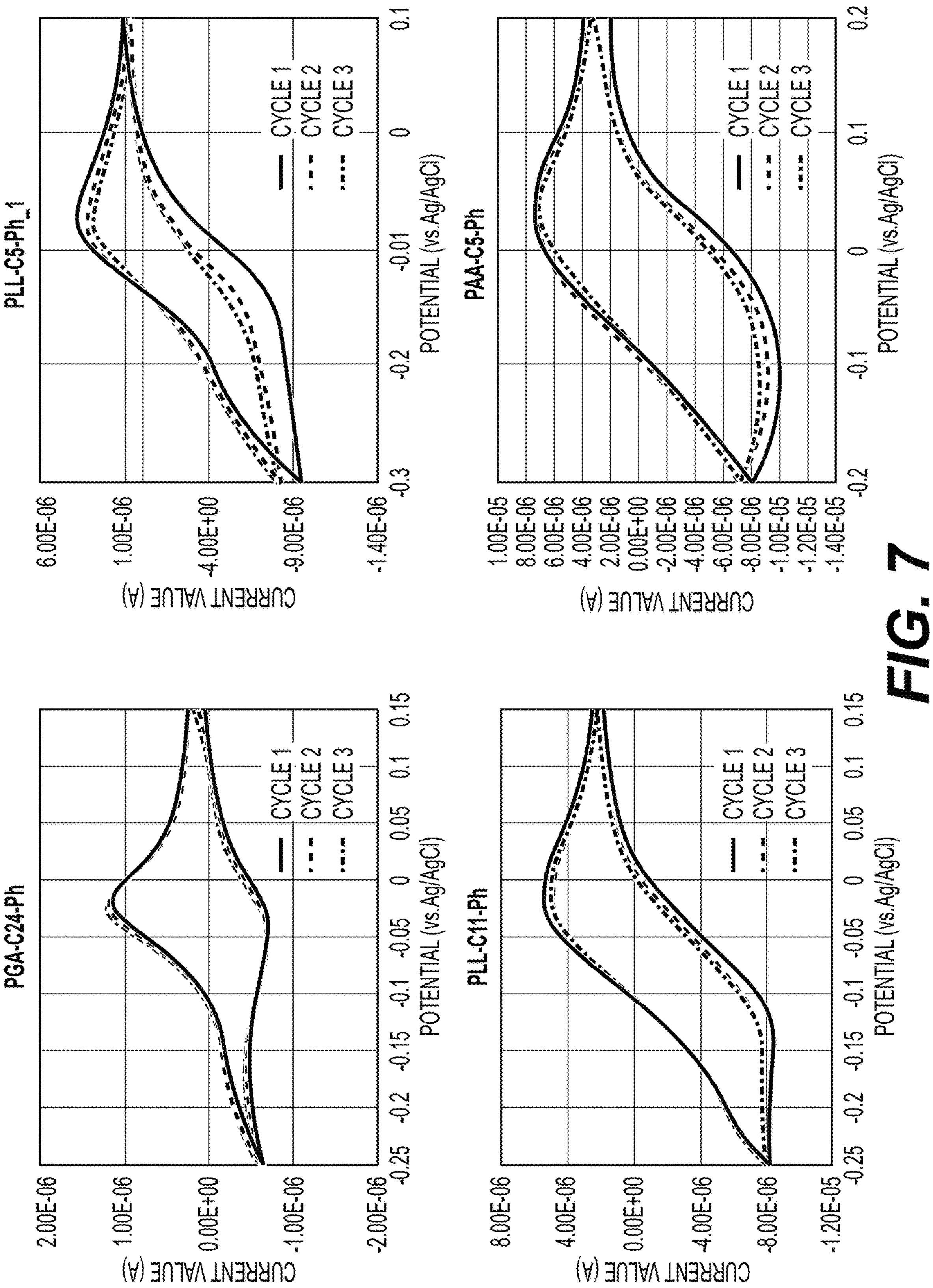
FIG. 7 is an example of a cyclic voltammogram of the present disclosure using a high molecular weight polymer to which a phenazine derivative is covalently bonded.
Figure 8:
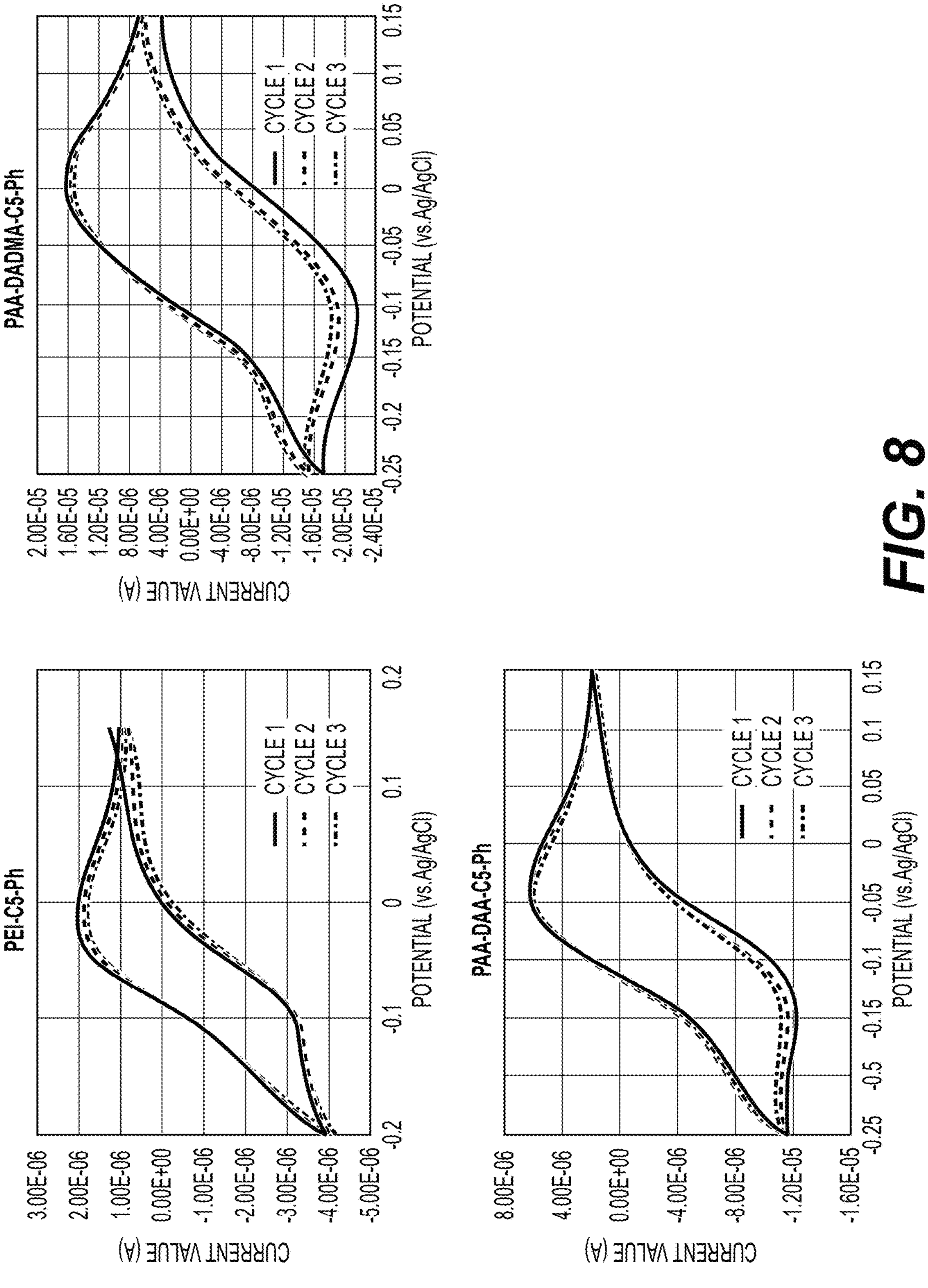
FIG. 8 is an example of a cyclic voltammogram of the present disclosure using a high molecular weight polymer to which a phenazine derivative is covalently bonded.
Figure 9:
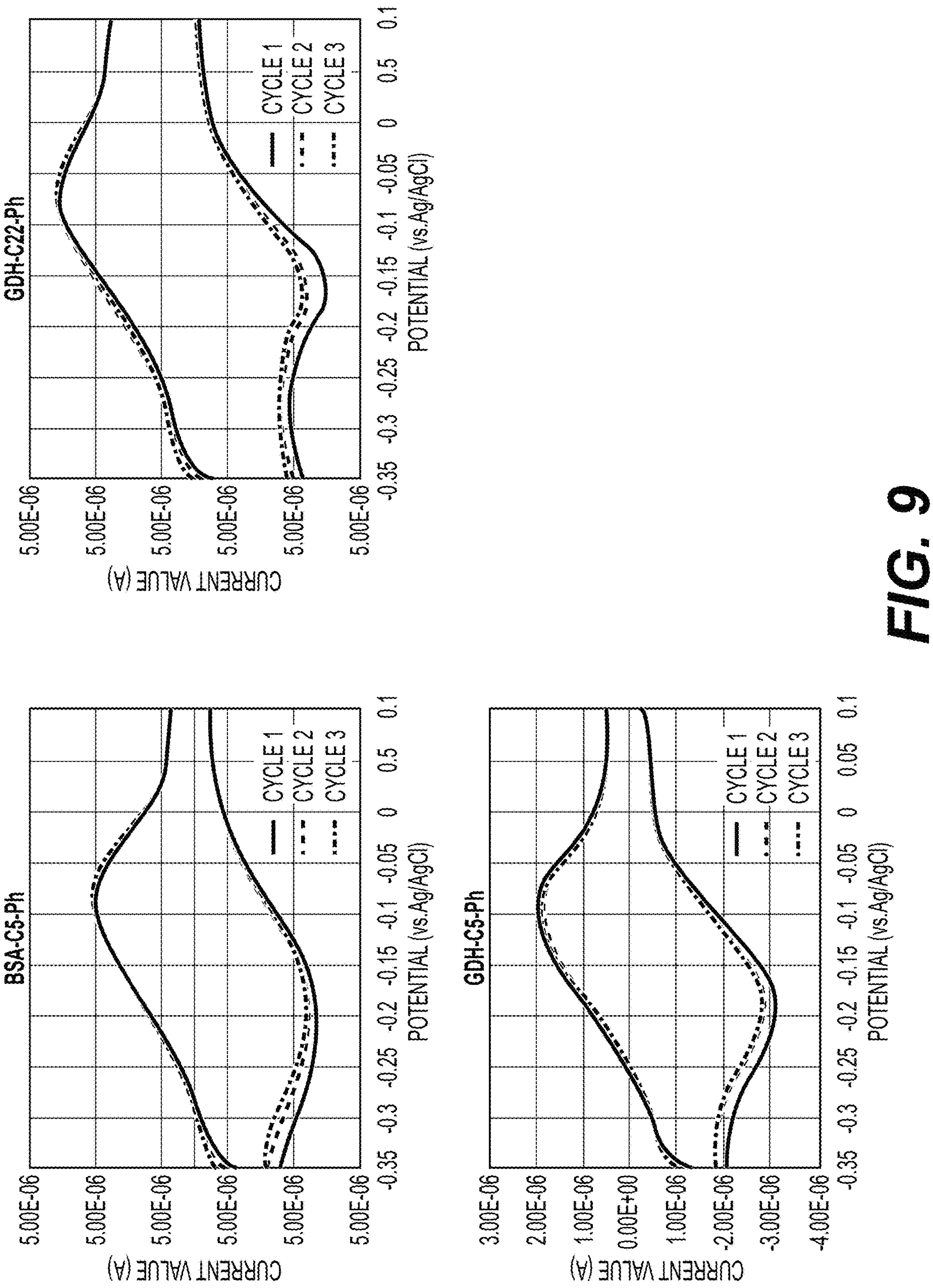
FIG. 9 is an example of a cyclic voltammogram of the present disclosure using a protein to which a phenazine derivative is covalently bonded.
Figure 10:
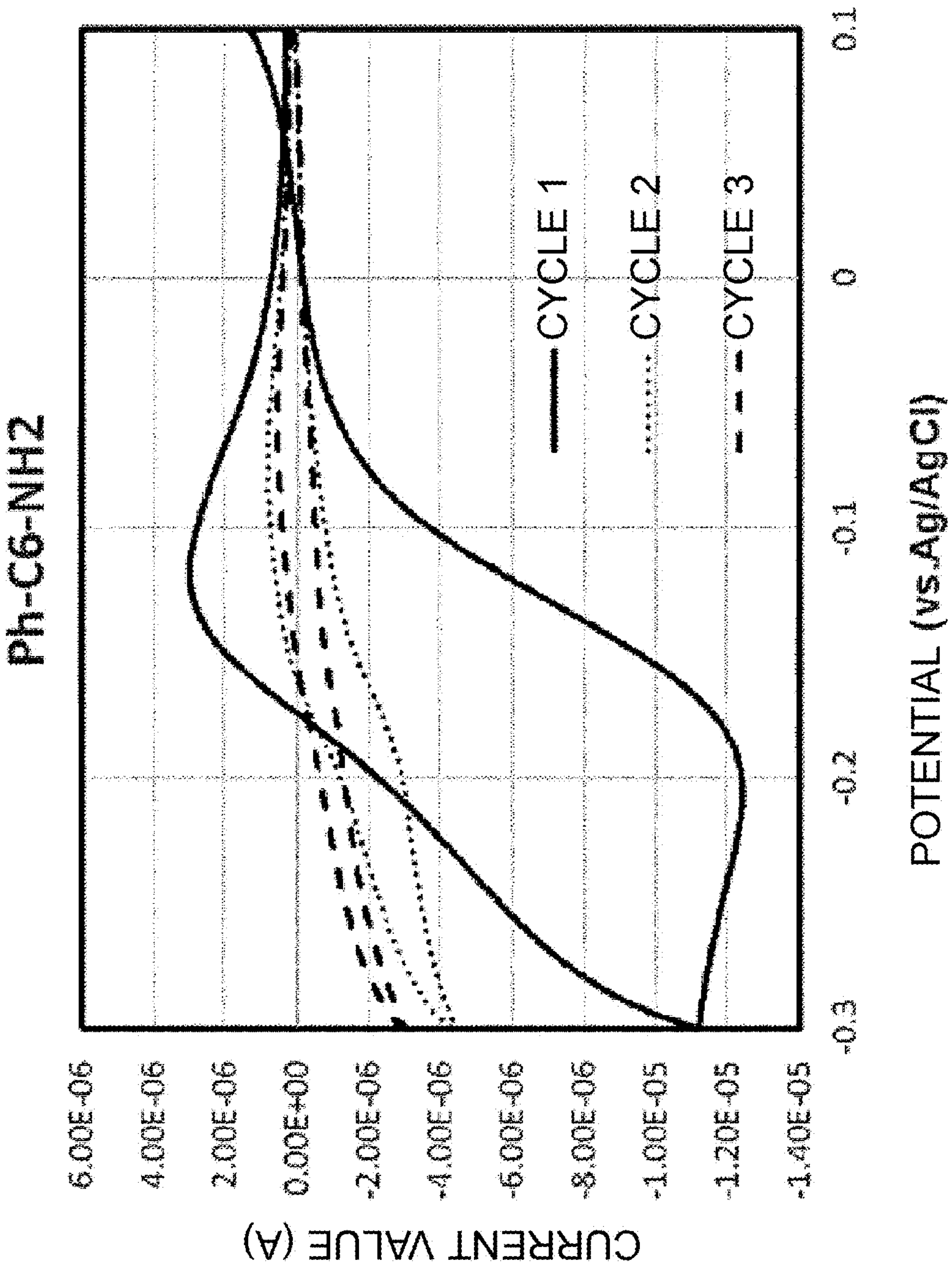
FIG. 10 is an example of a cyclic voltammogram of a phenazine derivative as a comparison.

These electrodes were immersed in PBS and made stationary at the initial potential for 10 seconds before potential sweep was initiated. The obtained cyclic voltammograms are shown in FIGS. 7 to 9.

In an electrode using the phenazine derivative Ph-C6-NH2 of Comparative Example 1 (a low molecular weight phenazine derivative having only the first' linker), which is not bonded to a high molecular weight polymer, oxidation peaks almost disappeared during Cycle 3. In contrast, oxidation peaks were maintained beyond Cycle 3 in electrodes using the high molecular weight redox polymer obtained in Examples 1 to 7, in which a phenazine derivative was bonded to various synthesized high molecular weight polymers. Oxidation peaks were maintained beyond Cycle 5 in electrodes using the high molecular weight redox polymers obtained in Examples 8 to 10, in which a phenazine derivative was bonded to various proteins.

These results indicate that low molecular weight phenazine derivatives leach out of the electrode, whereas leaching of phenazine derivatives out of the electrode was suppressed by bonding them to a high molecular weight polymer or a protein.

(2) Mediator Preservation Stability

Figure 11:
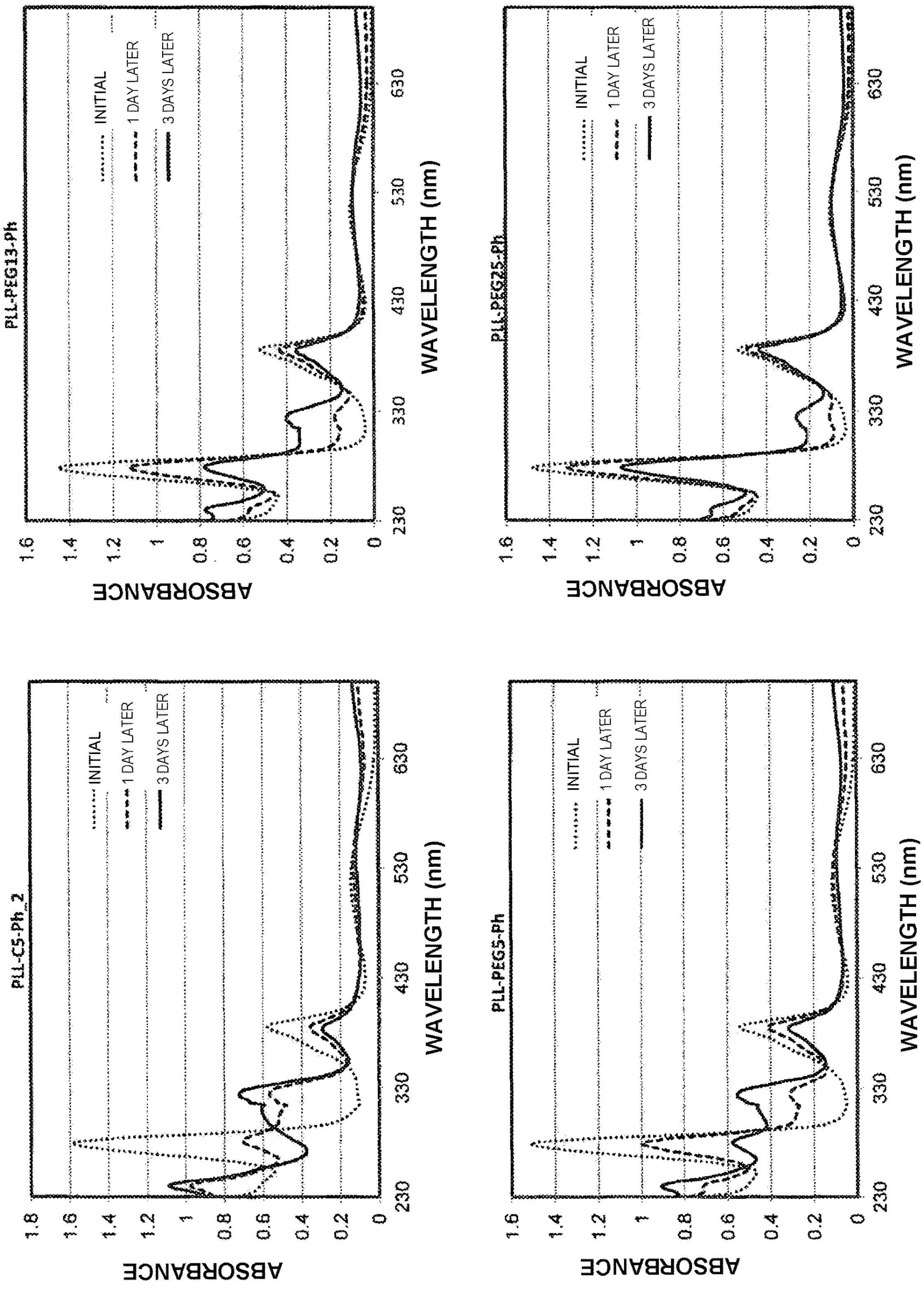
FIG. 11 shows absorption spectra of a high molecular weight polymer of the present disclosure to which a phenazine derivative is covalently bonded.

The absorption spectra of the high molecular weight redox polymers obtained in Examples 11 to 14 were measured at the initial stage of synthesis and after stored at 37° C. for one day and three days. Measurement was performed by adding 100 μL of a solution of each high molecular weight redox polymer to a microplate (Greiner Bio-One UV-STAR MICROPALLETE 96 WELL F-BODEN) using a plate reader (TECAN; Infinite M200 PRO). The absorbance was obtained by reducing the measured absorbance of PBS as a blank value. The obtained absorption spectra are shown in FIG. 11.

The changes in absorption peaks near 280 nm and 385 nm indicate that there are less changes in absorption peaks with a longer linker (in particular, PEG chains contained in general formulas (3) and general formula (9)), as observed with PLL-PEGS-Ph (Example 12: the linker main chain is composed of 31 atoms) and PLL-PEG13-Ph (Example 13: the linker main chain is composed of 55 atoms), PLL-PEG25-Ph (Example 14: the linker main chain is composed of 91 atoms), as compared with PLL-05-Ph 2 (Example 11: the linker main chain is composed of 10 atoms).

This result shows that the thermostability of redox mediators in a biological environment is improved by increasing the distance between the phenazine moiety and the high molecular weight polymer with the linker positioned therebetween.

(3) Measurement of Probe Characteristics

The glucose responsiveness and durability of a sensor prepared on a gold electrode with the following composition and procedure were evaluated.

<Preparation of Solutions>

(a) Enzyme/mediator Solution

A glucose dehydrogenase (FAD-dependent) (BBI International; GDH GLD1), 20% glutaraldehyde solution (Wako Pure Chemical Industries, Ltd.), and PLL-PEG25-Ph synthesized as in Example 14 were mixed to the final concentration for each reagent shown in Table 2, and the mixture was allowed to react for approximately 2 hours to obtain a high molecular weight redox polymer in which glucose dehydrogenase and PLL-PEG2-Ph were crosslinked.

TABLE 2

| Reagent | Final concentration |
| --- | --- |
| GDH GLD1 | 20000 U/mL |
| PLL-PEG25-Ph | Absorbance at 386 nm equivalent to 3.1 |
| Glutaraldehyde | 0.01% |

(b) Suspension of Carbon Pale Particle

Ketjen black EC600JD (Lion Specialty Chemicals Co., Ltd.) was suspended in Milli-Q water to a concentration of 2 mg/mL, and the suspension was treated with an ultrasonic homogenizer for 10 minutes or longer. If a few hours had passed after preparation of the suspension, the suspension was treated with the ultrasonic homogenizer again for approximately 10 minutes before use.

(c) Solution of Polymer for a Protective Film

Poly(4-vinylpyridine) (Mw=160,000) (Sigma-Aldrich) [P4VP] was dissolved in ethanol to a concentration of 10% (weight/volume) to prepare a P4VP ethanol solution.

<Preparation of Sensor>

In a volume of 0.5 μL of the ketjen black suspension was applied on the gold working electrode and dried for approximately 5 minutes. Application and drying were further repeated twice, that is, the ketjen black suspension was applied a total of three times. In a volume of 0.5 μL of the enzyme/mediator solution after the reaction for 2 hours was applied and dried for approximately 30 minutes. The electrode was further immersed in the P4VP ethanol solution, dried for 10 minutes, then immersed again, and dried for 30 minutes or longer to form a protective film and prepare a sensor.

<Electrochemical Measurement>

Figure 12:
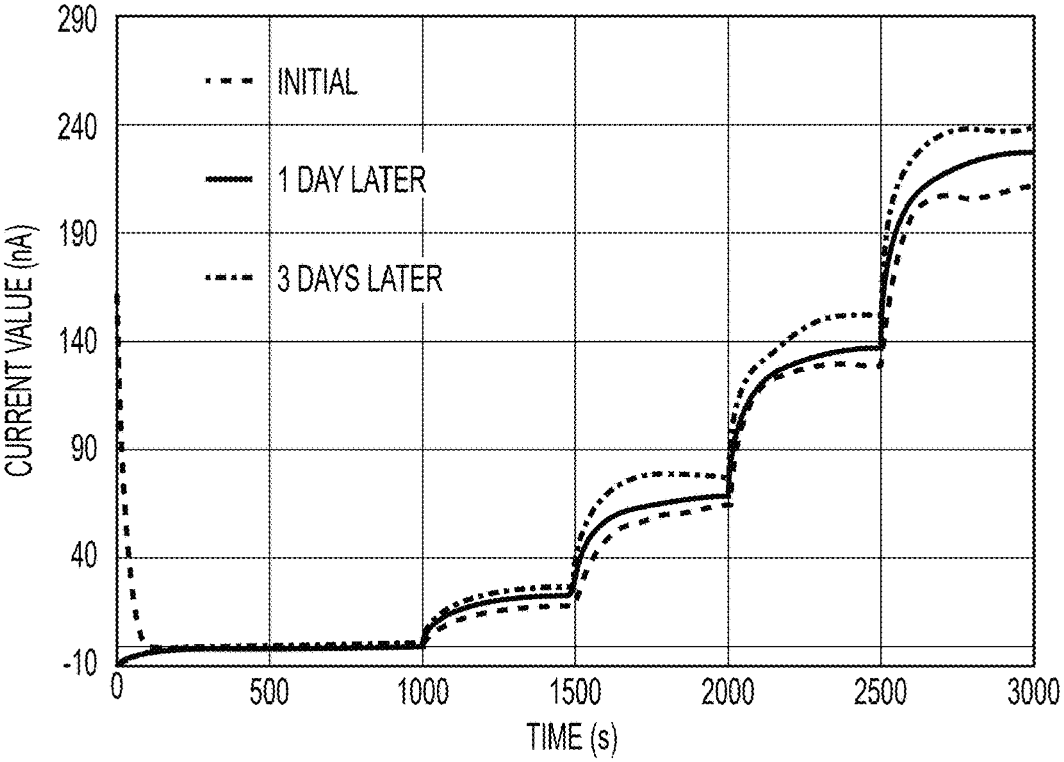
FIG. 12 is a graph showing glucose response characteristics of a probe using the high molecular weight polymer of the present disclosure to which a phenazine derivative is covalently bonded.
Figure 13:
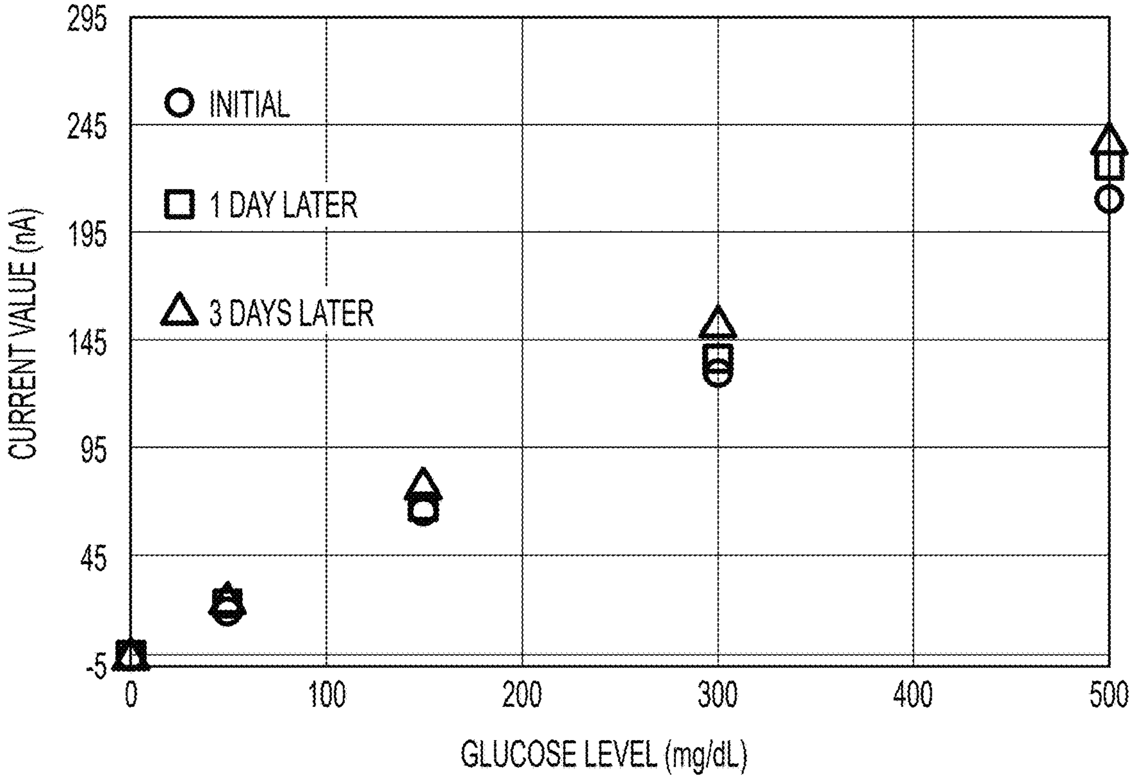
FIG. 13 is a graph showing the durability of a probe using the high molecular weight polymer of the present disclosure to which a phenazine derivative is covalently bonded.

A measurement for amperometric i-t curve was performed using a potentiostat (BAS Inc.) with three electrodes comprising the above-described sensor as a working electrode, a gold electrode as a counter electrode, and Ag/AgCl (saturated potassium chloride) (BAS Inc.) as a reference electrode while immersing the prepared sensor in PBS. Starting at 1000 seconds after the initiation of measurement, glucose was added every 500 seconds to concentrations of 50, 150, 300, and 500 mg/dL, and the current response value was continuously measured. After measurement, the sensor was preserved in PBS at 37° C., and similar measurement was performed after one day and three days of preservation. The respective measurement results are shown in FIGS. 12 and 13 and summarized in Table 3. Of note, the respective measurement data shown in FIG. 13 and Table 3 are the mean of the values measured at five timepoints of 10, 20, 30, 40, and 50 seconds immediately before the next addition of glucose after addition of glucose to be measured in FIG. 12.

TABLE 3

| | Current value (nA) | | |
| --- | --- | --- | --- |
| Amount of glucose added (mg/dL) | Day 0 | Day 1 | Day 3 |
| 0 | −0.6 | −1.2 | −0.6 |
| 50 | 19.1 | 22.1 | 26.6 |
| 150 | 66.1 | 68.2 | 78.3 |
| 300 | 130.2 | 136.8 | 154.0 |
| 500 | 211.4 | 227.8 | 238.8 |

A high linearity was observed at glucose concentrations 0 to 500 mg/dL, indicating favorable glucose responsiveness.

After preservation at 37° C. for three days, a high linearity was still observed at glucose concentrations of 0 to 500 mg/dL, and the current value did not decrease compared with the initial responses, indicating favorable durability.

INDUSTRIAL APPLICABILITY

The high molecular weight redox polymer and the biosensor using the same of the present disclosure can prevent or suppress leaching of a redox mediator (a phenazine derivative) out of a protective film because the redox mediator is bonded to a high molecular weight polymer. Therefore, preservation stability (durability) can be improved while measurement sensitivity is maintained.

REFERENCE SIGNS LIST

1 Embedded electrochemical glucose sensor
10 Main body
11 Probe
111 Insulating substrate
112 Conductive thin film
**112*a*** Working electrode region
**112*b*** Reference electrode region
**112*c*** Counter electrode region
113 Groove
114 Working electrode
115 Reference electrode
**116*a*, 116*b*** Insulating resist
117 Counter electrode
118 Reagent layer
119 Protective film
121 Sensing portion
122 Terminal portion
2 Living body

The invention claimed is:

1. A high molecular weight redox polymer represented by general formula (A1):

(A1)

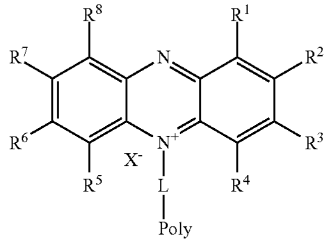

wherein $X^-$ represents an anionic species; L represents a linker comprising a chain having a plurality of atoms with at least one atom selected from the group consisting of a carbon atom, a nitrogen atom, an oxygen atom, and a sulfur atom; Poly represents a polymer having a weight-average molecular weight of 10,000 to 10,000,000; and $R^1$ to $R^8$ each independently represent a hydrogen atom, a halogen atom, a hydroxyl group, a carboxyl group, an amino group optionally having a substituent, a linear or branched, saturated or unsaturated hydrocarbon group having 1 to 6 carbon atoms and optionally having a substituent, an acyl group optionally having a substituent, an alkoxy group optionally having a substituent, or a phenyl group optionally having a substituent, wherein the optional substituent(s) on the amino group, hydrocarbon group, acyl group, alkoxy group and phenyl group is each independently selected from the group consisting of (a) a halogen atom, (b) a hydroxyl group, (c) a carboxyl group, (d) an amino group, (e) a $C_{1-6}$ linear or branched, saturated or unsaturated hydrocarbon group, (f) an acyl group, (g) an alkoxy group, (h) a carboxyl-alkyl group, (i) a mesyl group, and (k) a phenyl group.

2. The redox polymer according to claim 1, which is represented by general formula (B1):

(B1)

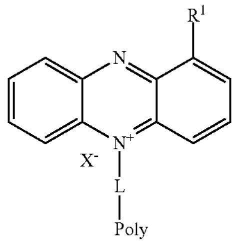

wherein $X^-$ represents an anionic species; L represents a linker comprising a chain having a plurality of atoms with at least one atom selected from the group consisting of a carbon atom, a nitrogen atom, an oxygen atom, and a sulfur atom; Poly represents the polymer having a weight-average molecular weight of 10,000 to 10,000,000; and $R^1$ represents a hydrogen atom, a halogen atom, a hydroxyl group, a carboxyl group, an amino group optionally having a substituent, a linear or branched, saturated or unsaturated hydrocarbon group having 1 to 6 carbon atoms and optionally having a substituent, an acyl group optionally having a substituent, an alkoxy group optionally having a substituent, or a phenyl group optionally having a substituent, wherein the optional substituent(s) on the amino group, hydrocarbon group, acyl group, alkoxy group and phenyl group is each independently selected from the group consisting of (a) a halogen atom, (b) a hydroxyl group, (c) a carboxyl group, (d) an amino group, (e) a $C_{1-6}$ linear or branched, saturated or unsaturated hydrocarbon group, (f) an acyl group, (g) an alkoxy group, (h) a carboxyl-alkyl group, (i) a mesyl group, and (k) a phenyl group.

3. The high molecular weight redox polymer according to claim 1, which is represented by general formula (1):

(1)

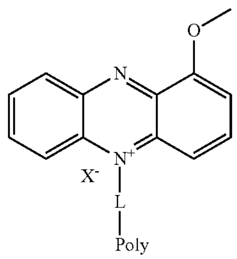

wherein $X^-$ represents an anionic species; L represents a linker comprising a chain having a plurality of atoms with at least one atom selected from the group consisting of a carbon atom, a nitrogen atom, an oxygen atom, and a sulfur atom; and Poly represents the polymer having a weight-average molecular weight of 10,000 to 10,000,000.

4. The redox polymer according to claim 1, wherein the formula (A1) is represented by formula (2):

(2)

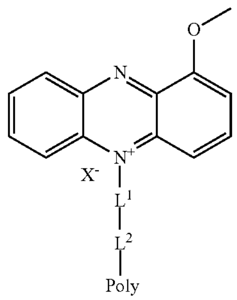

wherein, in formula (A1), L is represented by $L^1$ and $L^2$ in formula (2), and wherein, in formula (2), $X^-$ represents an anionic species; $L^1$ represents a first linker; $L^2$ represents a second linker; the first linker and the second linker each independently comprise a chain having a plurality of atoms with at least one atom selected from the group consisting of a carbon atom, a nitrogen atom, an oxygen atom, and a sulfur atom; and Poly represents the polymer having a weight-average molecular weight of 10,000 to 10,000,000.

5. The redox polymer according to claim 4, wherein the first linker and the second linker are bonded by a covalent bond.

6. The redox polymer according to claim 4, wherein the first linker comprises at least one of a polyethylene glycol chain and a hydrocarbon chain.

7. The redox polymer according to claim 6, wherein formula (2) is represented by formula (3):

(3)

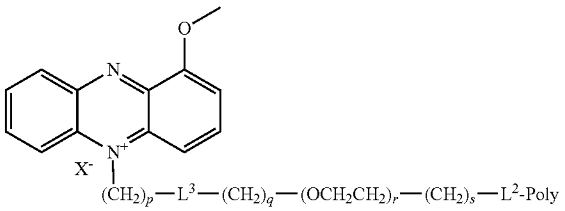

wherein, in formula (2), $L^1$ is represented by $(CH_2)_p$-$L^3$—$(CH_2)_q$—$(OCH_2CH_2)_r$—$(CH_2)_s$— in formula (3), wherein X represents an anionic species;

$L^3$ is not present or is —O—, —C(═O)—NH—or —NH—C(═O)—;

$L^2$ represents the second linker;

Poly represents the polymer having the weight-average molecular weight of 10,000 to 10,000,000;

p, q, and s are each independently an integer of 1 to 15; and r is an integer of 0 to 80.

8. The redox polymer according to claim 7, which is represented by formula (4):

(4)

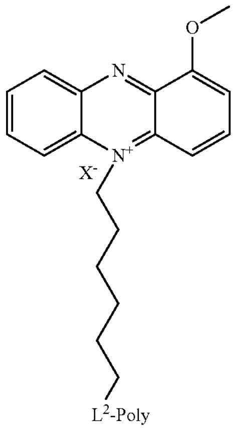

wherein $X^-$ represents an anionic species; $L^2$ represents the second linker; and Poly represents the polymer having the weight-average molecular weight of 10,000 to 10,000,000;

or formula (5):

(5)

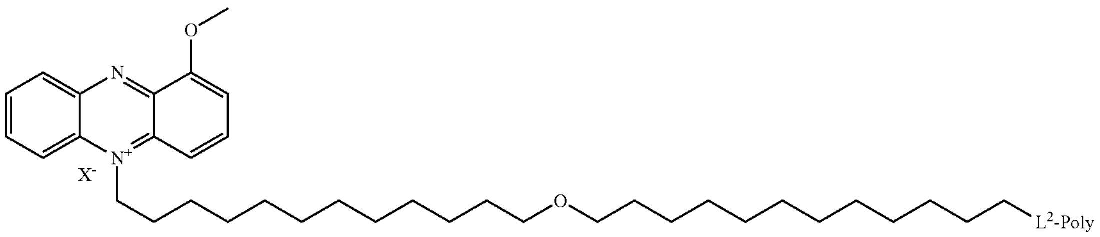

wherein $X^-$ represents an anionic species; $L^2$ represents the second linker; and Poly represents the polymer having the weight-average molecular weight of 10,000 to 10,000,000;

or formula (6):

(6)

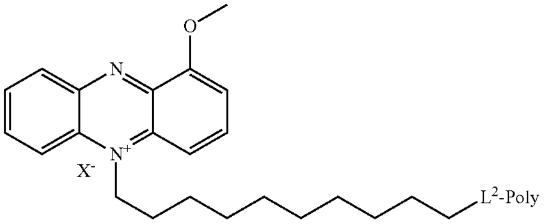

wherein $X^-$ represents an anionic species; $L^2$ represents the second linker; and Poly represents the polymer having the weight-average molecular weight of 10,000 to 10,000,000;

or formula (7):

(7)

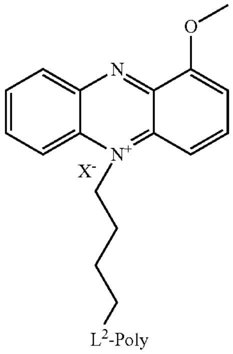

wherein $X^-$ represents an anionic species; $L^2$ represents the second linker; and Poly represents the polymer having the weight-average molecular weight of 10,000 to 10,000,000;

or formula (8):

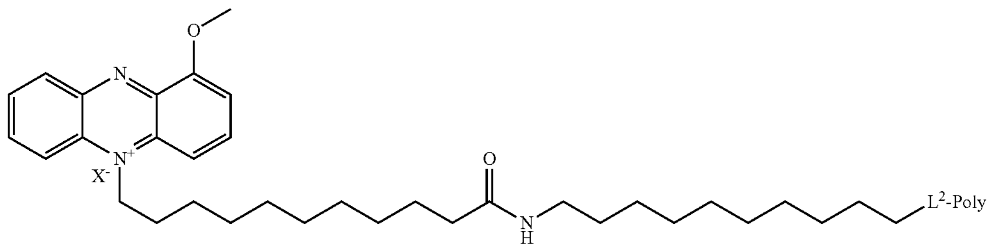

(8)

wherein $X^-$ represents an anionic species; $L^2$ represents the second linker; and Poly represents the polymer having the weight-average molecular weight of 10,000 to 10,000,000.

9. The hredox polymer according to claim 1, wherein a bond between atoms constituting the chain having the plurality of atoms is at least one bond selected from the group consisting of a carbon-carbon bond, an amide bond, and an ether bond.

10. The redox polymer according to claim 1, wherein the having a weight-average molecular weight of 10,000 to 10,000,000 is a polyamino acid-based polymer, a polyimine-based polymer, or an ethylene-based polymer.

11. The high molecular weight redox polymer according to claim 1, wherein the polymer having a weight-average molecular weight of 10,000 to 10,000,000 is a protein, a polypeptide, or a polynucleotide.

12. The redox polymer according to claim 1, wherein the anionic species is any one-selected from the group consisting of a halogen ion, an ion of a compound comprising halogen, a hydroxide ion, a carboxylate ion, a nitrate ion, a nitrite ion, an acetate ion, a hydrogen carbonate ion, a dihydrogen phosphate ion, a hydrogen sulfate ion, an alkyl sulfonate ion, a hydrogen sulfide ion, a hydrogen oxalate ion, a cyanate ion, and a thiocyanate ion.

13. The redox polymer according to claim 1, which is hydrophilic.

14. A redox polymer mixture, comprising a at least two redox polymers according to claim 1.

15. A biosensor for detecting or quantifying an analyte, comprising:

a working electrode, a counter electrode, a reagent layer disposed on the working electrode, and a protective film covering at least the reagent layer;

the reagent layer comprising an oxidoreductase that oxidizes or dehydrogenates the analyte and the redox polymer according to claim 1.

16. The biosensor according to claim 15, which has a reference electrode.

17. The biosensor according to claim 15, wherein the oxidoreductase is a coenzyme-binding enzyme.

18. The biosensor according to claim 17, wherein the oxidoreductase is crosslinked to the high molecular weight redox polymer.

19. The biosensor according to claim 15, wherein the analyte is glucose, and the oxidoreductase is glucose oxidase or glucose dehydrogenase.

20. The biosensor according to claim 19, wherein the glucose dehydrogenase is a flavin adenine dinucleotide (FAD)-dependent glucose dehydrogenase.

21. The biosensor according to claim 19, wherein the glucose dehydrogenase has an enzyme activity against maltose of 5% or lower when the enzyme activity against glucose is assumed to be 100%.

22. The biosensor according to claim 19, wherein the glucose dehydrogenase has an enzyme activity against maltose of 3% or lower when the enzyme activity against glucose is assumed to be 100%.

23. The biosensor according to claim 15, wherein the protective film has a pore for allowing an analyte existing outside the protective film to permeate into the protective film.

* * * * *